US012700505B2

(12) United States Patent (10) Patent No.: US 12,700,505 B2
Moretti et al. (45) Date of Patent: Aug. 4, 2026

(54) INTEGRATED DIAGNOSTIC IMAGING SYSTEM WITH AUTOMATED PROTOCOL SELECTION AND ANALYSIS

(71) Applicant: AI Optics Inc., New York City, NY (US)

(72) Inventors: Luke Michael Moretti, New York City, NY (US); Sagar Soni, Sunnyvale, CA (US)

(73) Assignee: AI Optics Inc., New York, NY (US)

( * ) Notice: Subject to any disclaimer, the term of this patent is extended or adjusted under 35 U.S.C. 154(b) by 0 days.

(21) Appl. No.: 18/755,288

(22) Filed: Jun. 26, 2024

(65) Prior Publication Data

US 2025/0022599 A1 Jan. 16, 2025

Related U.S. Application Data

(60) Provisional application No. 63/513,089, filed on Jul. 11, 2023.

(51) Int. Cl.
*G16H 40/67* (2018.01)
*G16H 50/20* (2018.01)
*G16H 70/60* (2018.01)

(52) U.S. Cl.
CPC ............. *G16H 50/20* (2018.01); *G16H 40/67* (2018.01); *G16H 70/60* (2018.01)

(58) Field of Classification Search
None
See application file for complete search history.

(56) References Cited

U.S. PATENT DOCUMENTS 5,912,720 A 6/1999 Berger
8,687,862 B2 4/2014 Hsu et al.
(Continued)

FOREIGN PATENT DOCUMENTS

JP 2020178903 11/2020
KR 20190091857 8/2019
(Continued)

OTHER PUBLICATIONS

Center for Innovation (L V Prasad Eye Institute), Open Indirect Ophthalmoscope, https://lvpmitra.com/oio#introduction (2021).
(Continued)

*Primary Examiner* — John A Pauls
(74) *Attorney, Agent, or Firm* — Knobbe Martens Olson & Bear LLP

(57) ABSTRACT

Disclosed in an integrated diagnostic imaging system (IDIS) designed to optimize the process of medical imaging and disease diagnosis. The IDIS can incorporate an intuitive disease selection interface that allows clinicians to select potential diseases of interest to screen for. Subsequently, a dynamic protocol selection algorithm can utilize a comprehensive imaging protocol database to determine the optimal imaging protocol corresponding to the selected diseases. The chosen protocols can be then executed by an imaging system, which can include different imaging modalities. Following the image acquisition, image analysis processes specific to the targeted diseases can process the images and identify pertinent features. The diagnostic results can be displayed in an intuitive and interactive results display, enhancing clinician interpretation and decision-making. The IDIS can streamline the diagnostic imaging workflow, facilitate accurate disease detection, and ensure adaptability to advancements in medical image analysis.

14 Claims, 6 Drawing Sheets

(56) References Cited

U.S. PATENT DOCUMENTS

| | | | |
|---|---|---|---|
| 9,757,031 B2 | 9/2017 | Wang et al. | |
| 10,376,142 B2 | 8/2019 | Dirghangi et al. | |
| 2005/0234300 A1 | 10/2005 | Farrell et al. | |
| 2009/0323021 A1* | 12/2009 | Uchida | A61B 3/12 |
| | | | 351/206 |
| 2011/0299036 A1 | 12/2011 | Goldenholz | |
| 2012/0257163 A1 | 10/2012 | Dyer et al. | |
| 2015/0081315 A1* | 3/2015 | Baker | G16H 30/20 |
| | | | 705/2 |
| 2018/0055357 A1 | 3/2018 | Meyerson et al. | |
| 2018/0153399 A1 | 6/2018 | Fink et al. | |
| 2019/0133435 A1 | 5/2019 | Browne et al. | |
| 2019/0216308 A1 | 7/2019 | Senaras et al. | |
| 2020/0170564 A1 | 6/2020 | Jiang et al. | |
| 2020/0196869 A1 | 6/2020 | Narayanan | |
| 2020/0294682 A1* | 9/2020 | Yoshida | G16H 80/00 |
| 2020/0405148 A1 | 12/2020 | Tran | |
| 2021/0035301 A1 | 2/2021 | Soares et al. | |
| 2022/0202384 A1* | 6/2022 | Saiki | G06F 3/0486 |
| 2022/0245811 A1 | 8/2022 | DiGiore et al. | |
| 2022/0246298 A1 | 8/2022 | Abulnaga et al. | |
| 2022/0280028 A1 | 9/2022 | Moretti et al. | |
| 2022/0405927 A1 | 12/2022 | Villard et al. | |
| 2023/0377112 A1* | 11/2023 | Neelavalli | G16H 30/40 |

FOREIGN PATENT DOCUMENTS

| | | |
|---|---|---|
| KR | 102032193 | 10/2019 |
| KR | 20190129247 | 11/2019 |
| WO | WO 2016/179370 | 11/2016 |
| WO | WO 2017/031099 | 2/2017 |
| WO | WO 2020/173516 | 9/2020 |

OTHER PUBLICATIONS

International Conference on Machine Learning, pp. 1321-1330. PMLR, 2017.

EyeNuk EyeArt screening system (https://www.eyenuk.com/en/) (retrieved in Mar. 2021).

Horus 100 fundus camera (http://www.miis.com.tw/product01.php?no=36) 2014.

Horus 200 portable fundus camera (http://www.miis.com.tw/product01.php?no=84) 2014.

IDx-DR Autonomous AI (https://dxs.ai/products/dermatology/autonomous-ai/) 2020.

IDx-DR Overview: Close Care Gaps, Prevent Blindness (https://dxs.ai/products/idx-dr/idx-dr-overview/) 2020.

Masumoto, et al, Deep-learning classifier with an ultrawide-field scanning laser ophthalmoscope detects glaucoma visual field severity, Glaucoma Journal 27(7):647-652 (2018).

Mediworks FC 161 hand-held fundus camera (https://www.mediworks.biz/en/product/handheld-fundus-camera-fc161).

Microclear Luna Fundus Camera (https://www.microcleartech.com/en/productInfo?p=hfc_v2) (retrieved in Mar. 2021).

Remidio NMFOP (https://www.remidio.com/fop.php) (retrieved in Mar. 2021).

Ting, et al., Artificial intelligence and deep learning in ophthalmology, Br J. Ophthalmol 103:167-175 (2019).

WelchAllyn Standard Ophthalmoscope (https://www.welchallyn.com/en/products/categories/physical-exam/eye-exam/ophthalmoscopes--traditional-direct/35v_standard_ophthalmoscope.html# ) 2018.

WelchAllyn PanOptic Brochure (2016).

WelchAllyn iExaminer (https://www.welchallyn.com/en/microsites/iexaminer.html) 2018.

* cited by examiner

INTEGRATED DIAGNOSTIC IMAGING SYSTEM WITH AUTOMATED PROTOCOL SELECTION AND ANALYSIS

CROSS-REFERENCE TO RELATED APPLICATIONS

This application claims priority to U.S. Provisional application 63/513,089, filed Jul. 11, 2023, titled "Integrated Diagnostic Imaging System With Automated Protocol Selection And Analysis," which is incorporated by reference in its entirety.

TECHNICAL FIELD

The present disclosure generally relates to systems and methods for streamlined medical imaging and diagnostics. The systems and methods generally pertain to the integration of advanced software processes, robust database management, and medical imaging devices (such as, retinal imaging devices) to enhance and expedite the processes of imaging protocol selection, image acquisition, data analysis, and diagnostic result display for medical diagnosis.

BACKGROUND

Medical imaging technologies, such as computed tomography (CT), magnetic resonance imaging (MRI), ultrasound, optical coherence tomography, and color photography, have become indispensable tools in clinical practice. These technologies allow healthcare professionals to visualize anatomical structures of the body and allow for better diagnosis, disease monitoring, and treatment planning.

Still, there exist several challenges with the current systems and methods of medical imaging, which can be resolved using the approaches described herein.

BRIEF DESCRIPTION OF DRAWINGS

Various aspects of the disclosure will now be described with regard to certain examples and implementations, which are intended to illustrate but not limit the disclosure.

Throughout the drawings, reference numbers can be re-used to indicate correspondence between referenced elements. The drawings are provided to illustrate example implementations described herein and are not intended to limit the scope of the disclosure.

SUMMARY

Figure 1:
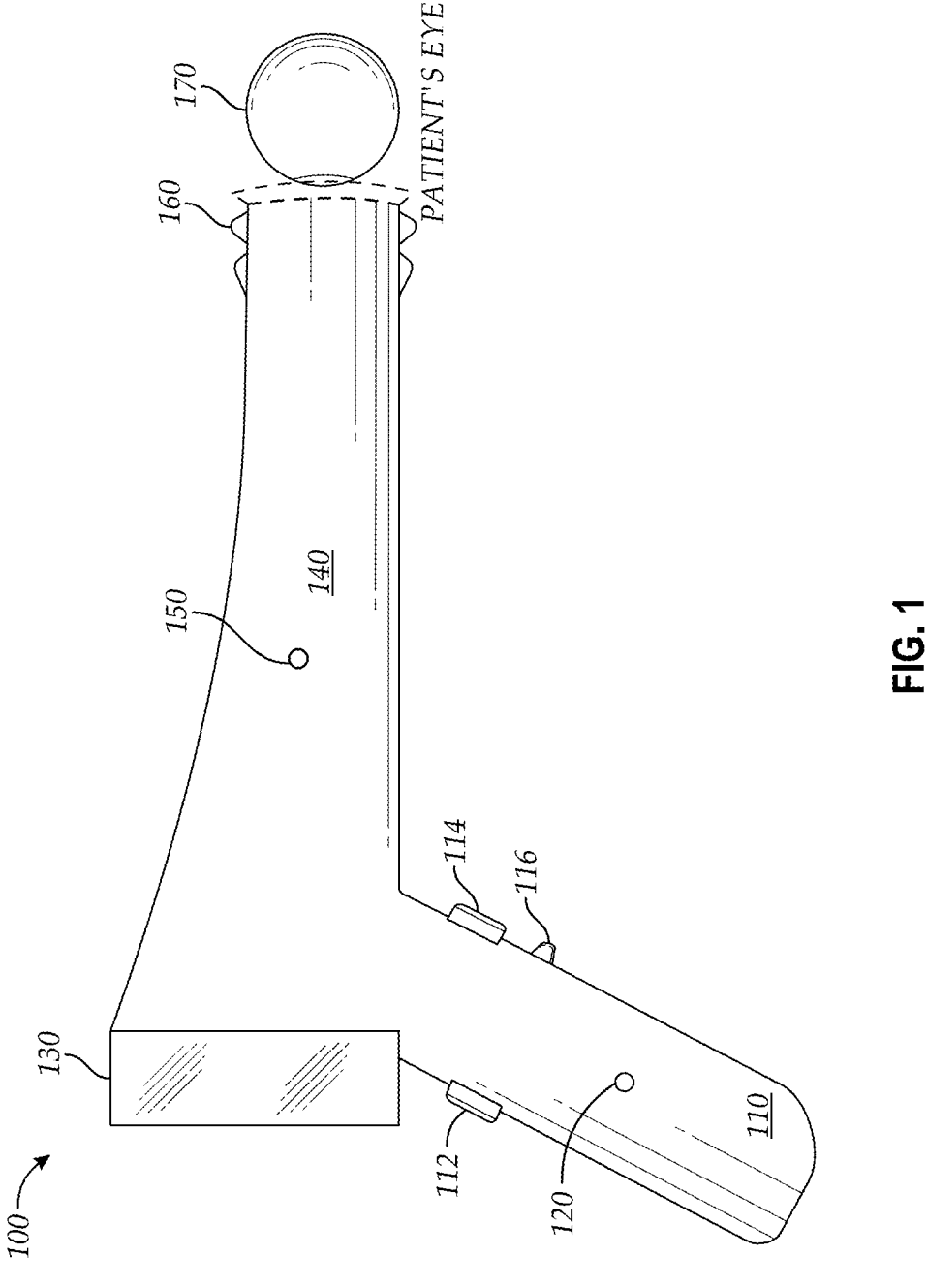
FIG. 1 illustrates an example retina camera.

The systems, methods, and devices described herein each have several aspects, no single one of which is solely responsible for its desirable attributes. Without limiting the scope of this disclosure, several non-limiting features will now be discussed briefly.

A retinal imaging method can include one or more of receiving one or more health selections from a user interface, determining a first disease and a second disease from a plurality of diseases based on the one or more health selections, identifying a first imaging protocol associated with the first disease and identifying a second imaging protocol associated with the second disease from a plurality of imaging protocols, generating a combined imaging protocol based on combining the first imaging protocol and the second imaging protocol, the combining can include removing a redundancy between the first and second imaging protocols, obtaining a plurality of images of a retina according to the combined imaging protocol, and providing an indication of a presence of the first disease and the second disease based on analyzing the plurality of images of the retina. The method can be performed by one or more processors.

The imaging method of any of the preceding paragraphs and/or any of the imaging methods described herein can include one or more of the following features. One or more health selections can include at least one symptom and the first and second diseases can be determined based on a user selecting the first and second diseases from the plurality of diseases manifesting the at least one symptom. The first imaging protocol can include a first sequence of images and the second imaging protocol can include a second sequence of images, and the redundancy can include an overlap between the first and second sequences of images. Identifying can include selecting the first imaging protocol from a first plurality of imaging protocols associated with the first disease and selecting the second imaging protocol from a second plurality of imaging protocols associated with the second disease, where the first and second imaging protocols can be selected responsive to determining that the overlap between the first and second imaging protocols exceeds overlaps between other pairs of imaging protocols from the first and second pluralities of imaging protocols.

The imaging method of any of the preceding paragraphs and/or any of the imaging methods described herein can include one or more of the following features. The indication of the presence of the first disease and the second disease can be performed by a classifier. The classifier can be a machine learning model configured to detect in the plurality of images one or more features relevant to the first disease and the second disease. The plurality of images can be obtained from a retinal imaging camera. The method can include displaying the indication on a display. The method can include communicating the indication to a remote computing system.

A medical imaging method can include one or more of receiving one or more health selections from a user interface, determining a first disease and a second disease from a plurality of diseases based on the one or more health selections, identifying a first imaging protocol associated with the first disease and identifying a second imaging protocol associated with the second disease from a plurality of imaging protocols, generating a combined imaging protocol based on combining the first imaging protocol and the second imaging protocol, the combining can include removing a redundancy between the first and second imaging protocols, with a plurality of imaging modalities, obtaining a plurality of images of a body part according to the combined imaging protocol, and providing an indication of a presence of the first disease and the second disease based on analyzing the plurality of images of the body part. The method can be performed by one or more processors.

The imaging method of any of the preceding paragraphs and/or any of the imaging methods described herein can include one or more of the following features. The plurality of imaging modalities can include a retinal imaging camera, a magnetic resonance imaging scanner, a computerized tomography scanner, or an optical coherence tomography camera. The redundancy can include at least one of changes between first and second imaging modalities of the plurality of imaging modalities, exposure to radiation from the plurality of imaging modalities, imaging duration with the plurality of imaging modalities, or arrangement of the plurality of imaging modalities based on clinical urgency. The one or more health selections can include at least one symptom, and the first and second diseases can be determined based on a user selecting the first and second diseases from the plurality of diseases manifesting the at least one symptom.

The imaging method of any of the preceding paragraphs and/or any of the imaging methods described herein can include one or more of the following features. The first imaging protocol can include a first sequence of images and the second imaging protocol can include a second sequence of images, and the redundancy can include an overlap between the first and second sequences of images. Identifying can include selecting the first imaging protocol from a first plurality of imaging protocols associated with the first disease and selecting the second imaging protocol from a second plurality of imaging protocols associated with the second disease, where the first and second imaging protocols can be selected responsive to determining that the overlap between the first and second imaging protocols exceeds overlaps between other pairs of imaging protocols from the first and second pluralities of imaging protocols.

The imaging method of any of the preceding paragraphs and/or any of the imaging methods described herein can include one or more of the following features. The indication of the presence of the first disease and the second disease can be performed by a classifier. The classifier can include a machine learning model configured to detect in the plurality of images one or more features relevant to the first disease and the second disease. The method can include displaying the indication on a display. The method can include communicating the indication to a remote computing system.

Disclosed is a non-transitory computer readable medium storing instructions that, when executed by one or more processors, cause the one or more processors to perform the imaging method of any of the preceding paragraphs and/or any of the imaging methods described herein.

DETAILED DESCRIPTION

The present system and methods relate to an integrated diagnostic imaging system (IDIS), which can use automation and artificial intelligence to enhance disease detection and improve diagnostic efficacy. For various purposes, enhancing disease detection and improving diagnostic efficacy is desirable.

Overview

Despite their immense utility, there exist several challenges with the current medical imaging systems and methods, which can be improved with advancements in technology. The decision of what imaging protocol to follow typically can depend on the judgment of the clinician or radiologist based on their understanding of the patient's symptoms, medical history, and suspected condition. This process can be time-consuming and subject to human error and variability, which can result in suboptimal imaging protocols. Furthermore, after the images are captured, the interpretation of these images to identify signs of disease requires a high degree of skill and experience, and even if a medical professional or radiologist analyzes them, there can be variability in interpretation between different professionals.

While the current system has served the medical community well, it presents a number of limitations and challenges, include one or more of the following.

Limited Customization: The 'one-size-fits-all' nature of current imaging protocols cannot account for the unique characteristics and needs of individual patients. This can lead to non-optimal imaging that can either miss important diagnostic features or be unnecessary.

Manual Selection: The selection and setup of optimal imaging protocols can often be performed manually, which can increase the likelihood of human error and inconsistencies. This can lead to the selection of suboptimal images acquired, such as acquiring an inadequate image (e.g., too few, lack of specific views, lack of specific sequences, etc.) or acquiring more images than necessary for a given patient's specific conditions of concern. Too many images being acquired can lead to unnecessary radiation exposure, such as in the case of modalities like CT, longer time spent performing the imaging protocol, and higher costs.

Dependence on Expert Interpretation: Image interpretation can be heavily reliant on the expertise of the interpreting professional, which can lead to variability in diagnostic outcomes. Additionally, the high demand for imaging interpretation can place a strain on healthcare resources.

Lack of Integration: Current systems can often lack seamless integration between the selection of diseases of interest, the imaging protocol, and the image interpretation process.

Thus, current practices in some fields of medical imaging have incorporated the use of pre-established 'quick orders' or 'protocols,' such as a 'stroke protocol' for MRI or a 'cancer screening protocol' for mammography. These predefined protocols standardize the imaging procedure for common conditions, which reduces the complexity of decision-making and help ensure that necessary images are captured in a consistent and reliable manner. This can certainly improve the efficiency and reproducibility of imaging procedures.

However, even these predefined protocols can still present several limitations. For one, many conditions and groups of conditions cannot have predefined protocol sets and, therefore, require the clinician to have knowledge of which protocols to perform based on which images and imaging techniques can provide the highest yield to the specific diseases of interest. Second, the predefined protocols cannot account for the presence of multiple diseases or conditions. In such cases, clinicians may need to manually select and order multiple protocols, which can be time-consuming and prone to errors. These multiple protocols stacked together cannot then be optimized for efficiency and can contain redundancies. Furthermore, these predefined protocols cannot contain a method for seamlessly updating as disease understanding and imaging techniques evolve. This can result in a potential loss of diagnostic accuracy or efficacy over time. Finally, the pre-existing protocols generally cannot interact dynamically with subsequent stages of the imaging-diagnostic process, such as the automated analysis and interpretation of the acquired images. As a result, the imaging and analysis processes can remain disjointed and potentially miss synergistic opportunities for improved diagnostic accuracy.

Given these challenges, there is a need for a system that can automatically select and implement an optimal imaging protocol based on the specific diseases of interest indicated by the clinician. One method can then use specialized algorithms to process and interpret the resulting images based on the diseases of interest and imaging protocols selected. Such a system can greatly improve the efficiency, accuracy, and patient-specificity of medical imaging, which can lead to better patient outcomes.

The disclosed systems and methods can overcome the aforementioned limitations by providing an integrated diagnostic imaging system (IDIS) that can be capable of dynamically selecting and sequencing imaging protocols based on selected diseases, including situations with multiple concurrent diseases. It can accommodate patient-specific factors, incorporate the latest disease-specific imaging techniques, and seamlessly interact with the image analysis component to optimize the entire imaging process from protocol selection to results display. The IDIS can revolutionize the current process of disease screening through medical imaging.

The foregoing aspects and many of the attendant advantages of this disclosure will become more readily appreciated as the same becomes better understood by reference to the following detailed description when taken in conjunction with the accompanying drawings.

Medical Diagnostics Devices with On-Board AI

A device with integrated artificial intelligence (AI) can be used to assess a patient's body part to detect a disease. The device can be portable or handheld by a user (which can be a patient or a healthcare provider). For example, the device can be a retina camera configured to assess a patient's eye (or retina) and, by using an on-board AI retinal disease detection system, provide real-time analysis and diagnosis of disease that caused changes to the patient's retina. Easy and comfortable visualization of the patient's retina can be facilitated using such retina camera, which can be placed over the patient's eye, display the retina image on a high-resolution display, potentially with screenshot capabilities, analyze a captured image by the on-board AI system, and provide determination of presence of a disease.

Such retina camera can perform data collection, processing, and diagnostics tasks on-board without the need to connect to another computing device or to cloud computing services. This approach can avoid potential interruptions of the clinical workflow when using cloud-based solutions, which involve transfer of data over the network and, accordingly, rely on network connectivity. This approach can facilitate faster processing because the device can continually acquire and process images without needing intermediary upload/download steps, which can be slow. Such retina camera can potentially improve accuracy (for instance, as compared to retina cameras that rely on a human to perform analysis), facilitate usability (for example, because no connectivity is used to transfer data for analysis or transfer results of the analysis), provide diagnostic results in real-time, facilitate security and guard patient privacy (for example, because data is not transferred to another computing device), or the like. Such retina camera can be used in many settings, including places where network connectivity is unreliable or lacking.

Such retina camera can allow for better data capture and analysis, facilitate improvement of diagnostic sensitivity and specificity, and improve disease diagnosis in patients. Existing fundus cameras can lack one or more of portability, display, on-board AI capabilities, etc. or require one or more of network connectivity for sharing data, another device (such as, mobile phone or computing device) to view collected data, rigorous training of the user, etc. In contrast, allowing for high-quality retinal viewing and image capturing with faster analysis and detection of the presence of disease via on-board AI system and image-sharing capabilities, the retina cameras described herein can potentially provide improved functionality, utility, and security. Such retina camera can be used in hospitals, clinics, and/or at home. The retina cameras or other instruments described herein, however, need not include each of the features and advantages recited herein but can possibly include any individual one of these features and advantages or can alternatively include any combination thereof.

As another example, the device can be an otoscope configured to assess a patient's ear and, by using an on-board artificial intelligence (AI) car disease detection system, possibly provide immediate analysis and/or diagnosis of diseases of the patient's ear. Such an otoscope can have one or more advantages described above or elsewhere in this disclosure. As yet another example, the device can be a dermatology scope configured to assess a patient's skin and, by using an on-board artificial intelligence (AI) skin disease detection system, possibly provide immediate analysis and/or diagnosis of diseases of the patient's skin. Such a dermatology scope can have one or more advantages described above or elsewhere in this disclosure.

FIG. 1 illustrates an example retina camera 100. A housing of the retina camera 100 can include a handle 110 and a body 140 (in some cases, the body can be barrel-shaped). The handle 110 can optionally support one or more of power source, imaging optics, or electronics 120. The handle 110 can also possibly support one or more user inputs, such as a toggle control 112, a camera control 114, an optics control 116, or the like. Toggle control 112 can be used to facilitate operating a display 130 in case of a malfunction. For example, toggle control 112 can facilitate manual scrolling of the display, switching between portrait or landscape mode, or the like. Toggle control 112 can be a button. Toggle control 112 can be positioned to be accessible by a user's thumb. Camera control 114 can facilitate capturing video or an image. Camera control 114 can be a button. Camera control 114 can be positioned to be accessible by a user's index finger (such as, to simulate action of pulling a trigger) or middle finger. Optics control 116 can facilitate adjusting one or more properties of imaging optics, such as illumination adjustment, aperture adjustment, focus adjustment, zoom, etc. Optics control 116 can be a button or a scroll wheel. For example, optics control 116 can focus the imaging optics. Optics control 116 can be positioned to be accessible by a user's middle finger or index finger.

The retina camera 100 can include the display 130, which can be a liquid crystal display (LCD) or other type of display. The display 130 can be supported by the housing as illustrated in FIG. 1. For example, the display 130 can be positioned at a proximal end of the body 140. The display 130 can be one or more of a color display, high resolution display, or touch screen display. The display 130 can reproduce one or more images of the patient's eye 170. The display 130 can allow the user to control one or more image parameters, such as zoom, focus, or the like. The display 130 (which can be a touch screen display) can allow the user to mark whether a captured image is of sufficient quality, select a region of interest, zoom in on the image, or the like. Any of the display or buttons (such as, controls, scroll wheels, or the like) can be individually or collectively referred to as user interface. The body 140 can support one or more of the power source, imaging optics, imaging sensor, electronics 150 or any combination thereof.

A cup 160 can be positioned on (such as, removably attached to) a distal end of the body 140. The cup 160 can be made at least partially from soft and/or elastic material for contacting patient's eye orbit to facilitate examination of patient's eye 170. For example, the cup can be made of plastic, rubber, rubber-like, or foam material. Accordingly, the cup 160 can be compressible. The cup 160 can also be disposable or reusable. In some cases, the cup 160 can be sterile. The cup 160 can facilitate one or more of patient comfort, proper device placement, blocking ambient light, or the like. Some designs of the cup can also assist in establishing proper viewing distance for examination of the eye and/or pivoting for panning around the retina.

Figure 2:
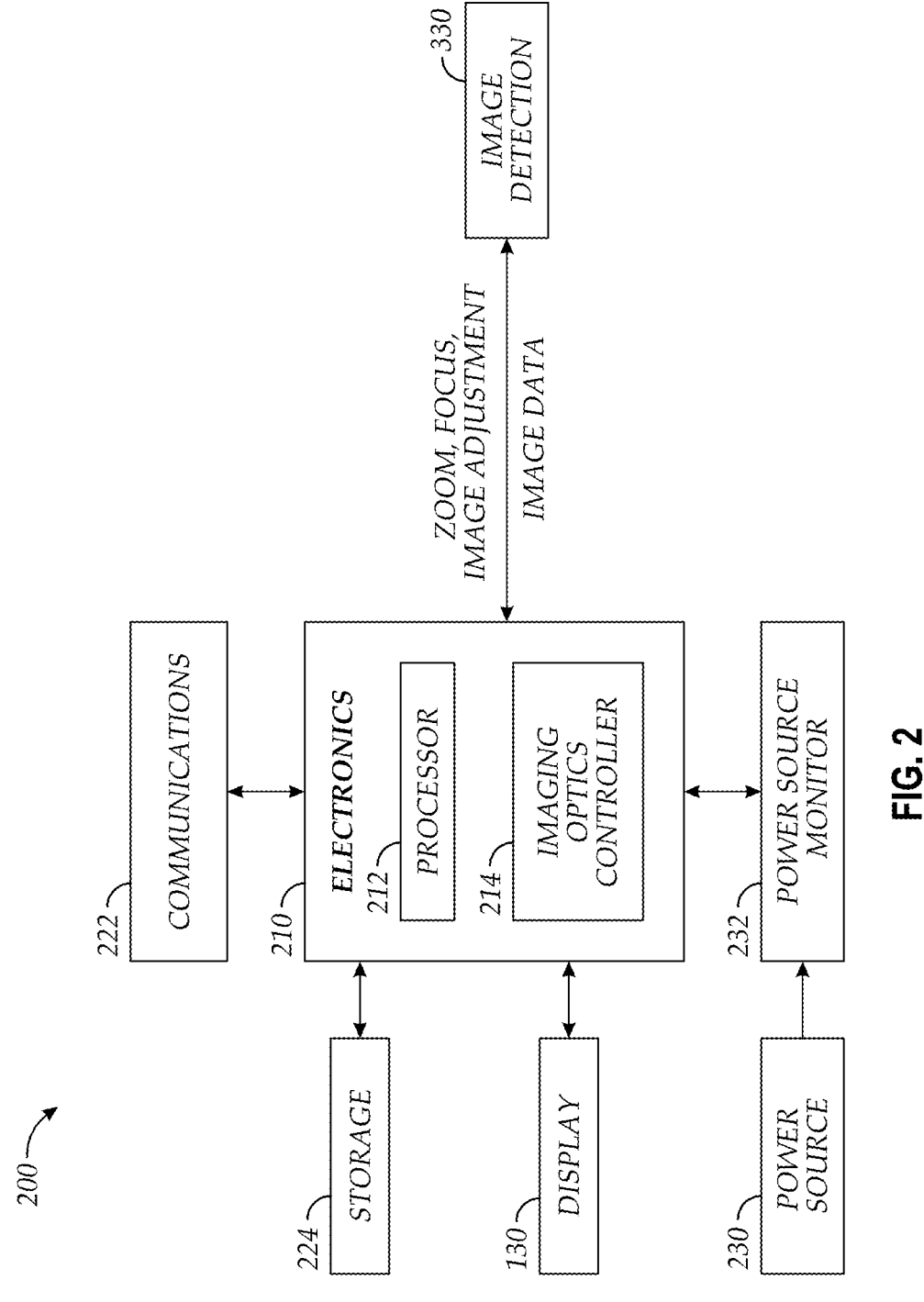
FIG. 2 illustrates a block diagram of various components of the retina camera.

FIG. 2 illustrates a block diagram 200 of various components of the retina camera 100. Power source 230 can be configured to supply power to electronic components of the retina camera 100. Power source 230 can be supported by the handle 110, such as positioned within or attached to the handle 110 or be placed in another position on the retina camera 100. Power source 230 can include one or more batteries (which can be rechargeable). Power source 230 can receive power from a power supply (such as, a USB power supply, AC to DC power converter, or the like). Power source monitor 232 can monitor level of power (such as, one or more of voltage or current) supplied by the power source 230. Power source monitor 232 can be configured to provide one or more indications relating to the state of the power source 230, such as full capacity, low capacity, critical capacity, or the like. One or more indications (or any indications disclosed herein) can be visual, audible, tactile, or the like. Power source monitor 232 can provide one or more indications to electronics 210.

Electronics 210 can be configured to control operation of the retina camera 100. Electronics 210 can include one or more hardware circuit components (such as, one or more controllers or processors 212), which can be positioned on one or more substrates (such as, on a printed circuit board). Electronics 210 can include one or more of at least one graphics processing unit (GPU) or at least one central processing unit (CPU). Electronics 210 can be configured to operate the display 130. Storage 224 can include memory for storing data, such as image data obtained from the patient's eye 170, one or more parameters of AI detection, or the like. Any suitable type of memory can be used, including volatile or non-volatile memory, such as RAM, ROM, magnetic memory, solid-state memory, magnetoresistive random-access memory (MRAM), or the like. Electronics 210 can be configured to store and retrieve data from the storage 224.

Communications system 222 can be configured to facilitate exchange of data with another computing device (which can be local or remote). Communications system 222 can include one or more of antenna, receiver, or transmitter. In some cases, communications system 222 can support one or more wireless communications protocols, such as WiFi, Bluetooth, NFC, cellular, or the like. In some instances, the communications system can support one or more wired communications protocols, such as USB. Electronics 210 can be configured to operate communications system 222. Electronics 210 can support one or more communications protocols (such as, USB) for exchanging data with another computing device.

Electronics 210 can control one or more imaging devices 330, which can be configured to facilitate capturing of (or capture) image data of the patient's eye 170. Electronics 210 can control one or more parameters of the imaging devices 330 (for example, zoom, focus, aperture selection, image capture, provide image processing, or the like). Such control can adjust one or more properties of the image of the patient's eye 170. Electronics 210 can include an imaging optics controller 214 configured to control one or parameters of the imaging devices 330. Imaging optics controller 214 can control, for example, one or more motor drivers of the imaging devices 330 to drive motors (for example, to select an aperture, to select lenses that providing zoom, to move of one or more lenses to provide autofocus, to move a detector array or image sensor to provide manual focus or autofocus, or the like). Control of one or more parameters of the imaging devices 330 can be provided by one or more of user inputs (such as a toggle control 112, a camera control 114, an optics control 116, or the like), display 130, etc. Imaging devices 330 can provide image data (which can include one or more images) to electronics 210. As disclosed herein, electronics 210 can be supported by the retina camera 100. Electronics 210 can not be configured to be attached to (such as, connected to) another computing device (such as, mobile phone or server) to perform determination of presence of a disease.

Disease Identification Through Image Analysis

Electronics 210 can include one or more controllers or processors (such as, a processor 212), which can be configured to analyze one or more images to identify a disease. For example, electronics 210 can include a processing system (such as, a Jetson Nano processing system manufactured by NVIDIA or a Coral processing system manufactured by Google), a System-on-Chip (SoC), or a Field-Programmable Gate Array (FPGA) to analyze one or more images. One or more images (or photographs) or video can be captured, for example, by the user operating the camera control 114 and stored in the storage 224. One or more prompts can be output on the display 130 to guide the user (such as, "Would you like to capture video or an image?"). Additionally or alternatively, symbols and graphics can be output on the display 130 to guide the user. Image quality can be verified before or after processing the one or more images or storing the one or more images in the storage 224. If any of the one or more images is determined to be of poor quality (for instance, as compared to a quality threshold), the image can not be processed or stored, the user can be notified, or the like. Image quality can be determined based on one or more of brightness, sharpness, contrast, color accuracy, distortion, noise, dynamic range, tone reproduction, or the like.

One or more preset modes can facilitate easy and efficient capture of multiple images or video. Such one or more preset modes can automatically focus, capture, verify image quality, and store the video or image(s). For some designs the one or more preset modes can switch one or more settings (such as, switch the light source to infrared light), and repeat this cycle without user intervention. In some designs, for example, a preset mode can facilitate obtaining multiple images for subsequent analysis. Such multiple images, for example, can be taken from different angles, use different light sources, or the like. This feature can facilitate automatically collecting an image set for the patient.

The user can select a region of an image for analysis, for instance, by outlining the region on the touch screen display 130, zooming in on region of interest on the display 130, or the like. In some cases, by default the entire image can be analyzed.

One or more machine learning models (sometimes referred to as AI models) can be used to analyze one or more images or video. One or more machine learning models can be trained using training data that includes images or video of subjects having various diseases of interest, such as retina disease (retinopathy, macular degeneration, macular hole, retinal tear, retinal detachment, or the like), ocular disease (cataracts or the like), systemic disease (diabetes, hypertension, or the like), Alzheimer's disease, etc. For example, any of the machine learning models can include a convolution neural network (CNN), decision tree, support vector machine (SVM), regressions, random forest, or the like. One or more machine learning models processing such images or videos can be used for tasks such as classification, prediction, regression, clustering, reinforcement learning, dimensionality reduction. Training of one or more models can be performed using many annotated images or video (such as, thousands of images or videos, tens of thousands of images or videos, hundreds of thousands of images or videos, or the like). Training of one or more models can be performed external to the retina camera 100. Parameters of trained one or more machine learning models (such as, model weights) can be transferred to the retina camera, for example, via retina camera's wireless or wired interface (such as, USB interface). Parameters of one or more models can be stored in the storage 224 (or in another memory of electronics 210). Output of the analysis (sometimes referred to as a diagnostic report) can include one or more of determination of the presence of disease(s), severity of disease(s), character of disease(s), clinical recommendation(s) based on the likelihood of presence or absence of disease(s). A diagnostic report can be displayed on the display 130. The diagnostic report can be stored in electronic medical record (EMR) format, such as EPIC EMR, or other document format (for example, PDF). The diagnostic report can be transmitted to a computing device. In some cases, the diagnostic report but not image data can be transmitted to the computing device, which can facilitate compliance with applicable medical records regulations (such as, HIPPA, GDPR, or the like).

One or more machine learning models can determine the presence of a disease based on the output of one or more models satisfying a threshold. As described herein, images or videos can be analyzed by one or more machine learning models one at a time or in groups to determine presence of the disease. For instance, the threshold can be 90%. When images are analyzed one at a time, determination of presence of the disease can be made in response to output of one or more models satisfying 90%. When images are analyzed in a group, determination of presence of the disease can be made in response to combined outputs of one or more models analyzing the group of images satisfying 90%.

In addition to these machine learning models, an Explainable AI framework (XAI) can be used to enhance the transparency and interpretability of the disease identification process. The XAI model can provide clear, understandable reasoning behind the AI model's decisions, enhancing trust in the system and facilitating the medical practitioner's understanding of the basis for the AI's disease identification. The explanatory components can include visual saliency maps indicating areas of importance, textual explanations highlighting key features leading to the prediction, or a combination of both. The explain ability feature may also help in identifying bias in AI model predictions, ensuring the robustness of the system.

The user can provide information (or one or more tags) to increase accuracy of the analysis by one or more machine learning models. For example, the user can identify any relevant conditions, symptoms, or the like that the patient (and/or one or more patient's family members) has been diagnosed with or has experienced. Relevant conditions can include systemic disease, retinal disease, ocular disease, or the like. Relevant symptoms can include blurry vision, vision loss, headache, or the like. Symptom timing, severity, or the like can be included in the identification. The user can provide such information using one or more user interface components on the display 130, such as a drop-down list or menu. One or more tags can be stored along with one or more pertinent images in the storage 224. One or more tags can be used during analysis by one or more machine learning models during analysis and evaluation. One or more images along with one or more tags can be used as training data.

In some cases, the diagnostic report can alternatively or additionally provide information indicating increased risk of disease or condition for a physician's (such as, ophthalmologist's) consideration or indicating the presence (or absence) of disease of condition. Physician can use this information during subsequent evaluation of the patient. For example, the physician can perform further testing to determine if one or more diseases are present.

Image or video analysis, including the application of one or more machine learning models to one or more images or video, can be performed by execution of program instructions by a processor and/or by a specialized integrated circuit that implements the machine learning model in hardware.

Disclosed devices and methods can, among other things, make the process of retinal assessment comfortable, easy, efficient, and accurate. Disclosed devices and methods can be used in physician offices, clinics, emergency departments, hospitals, in telemedicine setting, or elsewhere. Unnecessary visits to a specialist healthcare provider (such as, ophthalmologist) can be avoided, and more accurate decisions to visit a specialist healthcare provider can be facilitated. In places where technological infrastructure (such as, network connectivity) is lacking, disclosed devices and methods can be used because connectivity is not needed to perform the assessment.

Video Capture and Analysis

In an example, every frame in a retinal video feed can be analyzed. In real-time, each frame can be fed through the image quality assessment and, subsequently, through a feature, disease, or condition detection (which can be implemented as one or more AI models). As another example, instead of individual frame analysis, the system could implement the concept of frame pooling where a defined group of frame is analyzed together. This group analysis could potentially identify subtle changes or patterns that might be missed when analyzing frames in isolation. The frames can be selected by taking into consideration the temporal, or sequential, position of the frames. Using the time-series information in addition to the information contained within the image data (such as, pixels) of the frame can increase the robustness of the one or more AI models. For example, for a given video of 5,000 frames, analysis can be performed in such a way that it: a) considers all 5,000 frames sequentially, b) considers a subset of the frames (such as, every other frame, groups of 10 frames or less of more, every 30th frame such that a frame is considered every minute for a video that includes 30 frames per second, or the like), while keeping the order, c) considers a subset of the frames with order being irrelevant (taking advantage of the knowledge that the frames belong to a times-series), or d) considers all frames as individual images, foregoing any temporal information and basing its resulting output on whether one or more features, diseases, or conditions are present in any particular frame. Those frames whose quality has been determined to be sufficient (such as, satisfying one or more thresholds) can be provided to the feature, disease, or condition detection.

In some implementations, one or more frames can undergo the feature, disease, or condition detection provided that the one or more frames have successfully passed the first step of image quality assessment (for instance, the verification that they are of sufficient quality). In some cases, disease, condition, or feature detection can be performed once the video (or live feed) is in focus, within a specific brightness range, absent of artifacts (such as, reflections or blurring), or the like. This verification can be performed before or after any pre-processing (such as, brightness adjustments or the like). For example, once there is a clear, in-focus view of the retina, the AI can automatically start analyzing frames for detection of features, diseases, or conditions. In some cases, if the video or live feed goes out of focus, the analysis for features, diseases, or conditions can cease until the video is back in focus. The image quality assessment that analyzes whether the device is in-focus (or absent of artifacts, etc.) can be separate (such as, separate processing or a module) from the detection of features, disease, or conditions. The image quality assessment that analyzes whether the device is in focus can display or relay information to the user to help improve the focus.

There can be processing or a module (which can be separate from or part of the image quality assessment) that aids in the maintenance of focus or specific video or frame characteristics (such as, brightness, artifacts, etc.). For example, once the retina comes into focus, there can be a software or hardware module that automatically adjusts the focus of the image and/or imaging optics to maintain the focused retinal image. Assessment of the movement during the video recording process can be performed and correction for the motion can be made, for example, by using a machine learning (ML) model that processes the captured images.

An indication can be provided to the user when the video (or frames) is of sufficient quality based on the image quality assessment. The indication can be one or more of visual, audible, tactile, or the like. For example, a green ring (or another indication) can appear around the outside edge of the retinal video feed when the frames (such as, any of the frames from a group of frames or all of the frames from a group of frames) are passing the image quality assessment. In another example, a green dot or other indication, such as text, can appear on a display of the imaging device. The indication can be provided in real-time. An indication can be provided to the user when one or more features, diseases, or conditions are present or the probability for the presence of the features, diseases, or conditions. The indication can be provided in real-time.

Integrated Diagnostic Imaging System

Figure 3:
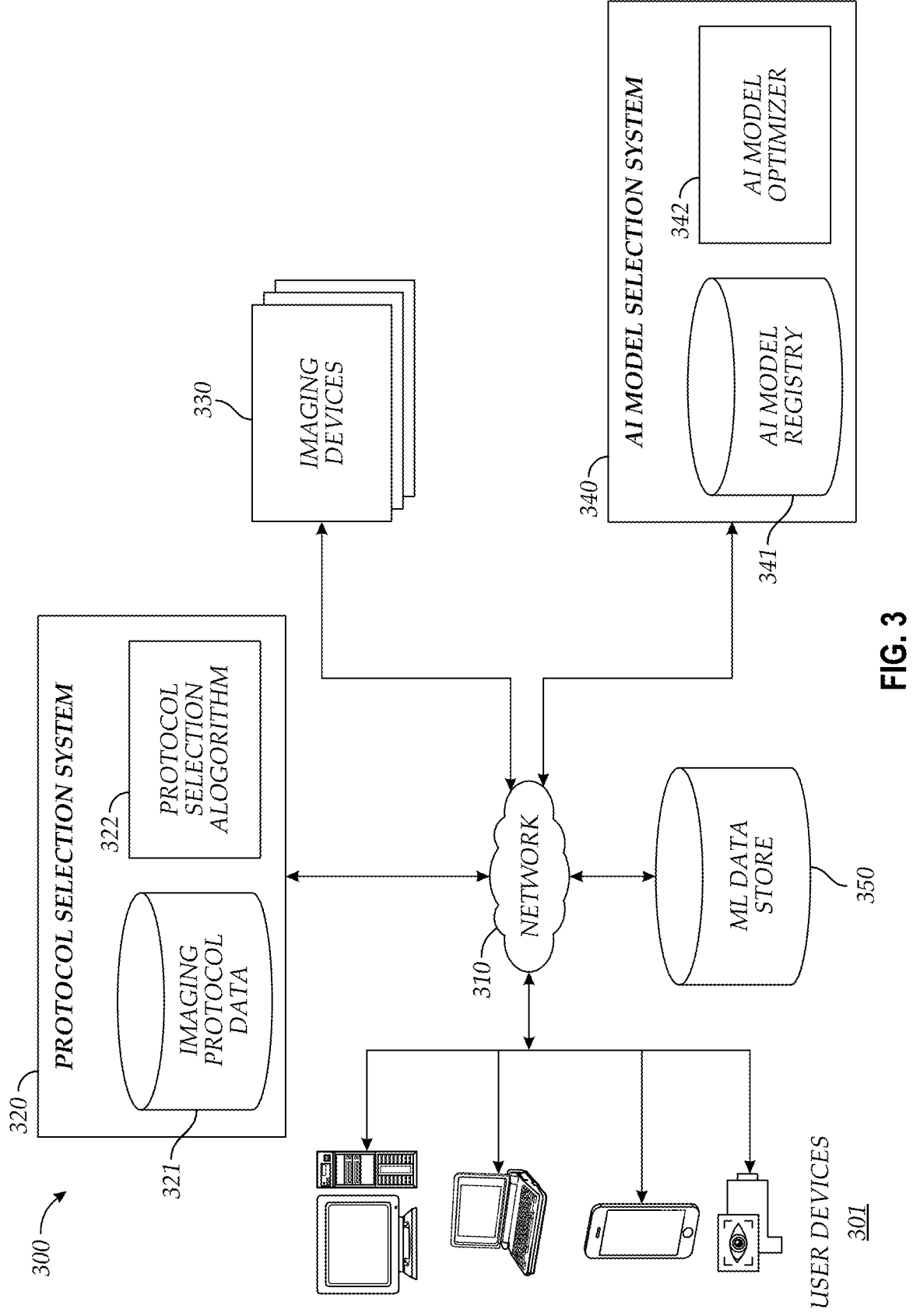
FIG. 3 is a block diagram of an illustrative integrated diagnostic imaging system (IDIS) in which the optimal protocols, imaging devices, and processing algorithms are determined for selected diseases.

FIG. 3 is a block diagram of an illustrative IDIS 300 in which the optimal protocols, one or more imaging devices 330, and processing algorithms are determined for selected diseases. The system, designed to augment the clinician's capability and provide a comprehensive and efficient diagnostic solution, involves a synergy of different components: a disease selection interface (DSI 410), a protocol selection system 320, an imaging system with imaging devices 330, and an AI model selection system 340 with image analysis algorithms. Within the protocol selection system 320 can include an imaging protocol database 321 and a protocol selection algorithm 322. Within the AI model selection system 340 can include an AI model registry 341 and an AI model optimizer 342. The results of the diagnosis of the medical imaging can be displayed on a results display 600, which can be implemented within one of the Imaging devices 330, the same user device 301 as the DSI 410, or another system. The various components of the illustrative IDIS 300 can communicate with each other via a network 310, which can communicate remotely or locally.

The DSI 410 can act as the entry point into the illustrative IDIS 300 by enabling clinicians to choose various health selections, such as but not limited to diseases, specific signs, or symptoms for evaluation. The DSI 410 can be standalone or integrated with an Electronic Health Record (EHR) system via the network 310 to provide a user-friendly interface with a differential diagnosis engine that promotes an efficient disease selection mechanism to generate the appropriate imaging protocols.

The protocol selection system 320 can input the diseases determined from the health selections from the DSI 410 to identify a combined imaging protocol through the imaging protocol database 321 and protocol selection algorithm 322. The imaging protocol database 321 can house data related to optimal imaging protocols for each disease to facilitate quick retrieval of relevant information through a robust database management system (DBMS) and can be stored locally or remotely. It can be configured for easy updates as clinical knowledge and technologies (both imaging and AI-diagnostics) advance and ensures strict control over data access. The protocol selection algorithm 322 can then interact with the disease selections from the DSI 410 and the imaging protocol database 321 to identify imaging protocols for diseases determined based on the health selections. The protocol selection algorithm 322 can be an intelligent algorithm, which can be performance-oriented so that an algorithm can optimize and implement the most efficient imaging protocols from the DSI 410 by reducing and/or removing redundancy in the combined imaging protocol based on the imaging modality and disease(s) of interest determined from the imaging protocol database 321.

The imaging system, which can be various imaging devices 330, such as the retina camera 100 in FIG. 1, can capture one or more images based on the combined imaging protocol and/or one or more protocols determined by the protocol selection algorithm 322. The imaging devices 330 can encompass various imaging modalities to increase the system's versatility. The system can be equipped with a computerized control system, such as the system described in FIG. 2, to ensure high-quality images are captured for accurate disease detection and to maintain interoperability with other components of the illustrative IDIS 300.

Within the AI model selection system 340, the AI model registry 341 can function in conjunction with the image analysis algorithms in an AI model optimizer 342, which can leverage advanced machine learning techniques, for example, deep learning, to autonomously detect the diseases of interest in the images acquired by the imaging system. The machine learning techniques can be stored either remotely or locally in an ML database 350. The AI model optimizer 342 can optimally select and utilize specific image analysis algorithms stored in the AI model registry 341, wherever applicable, based on the specific diseases of interest. The AI model registry 341, and the AI model selection system 340, can be adaptable for new disease-detection models and model updates.

The results display 600 can present diagnostic results in a clear, intuitive, and actionable format to the clinician. The results display 600 can be displayed on the user devices 301 used for the DSI 410, the imaging devices 330, and/or a separate system (such as, a remote computing device). It can be a user-friendly interface that can be equipped with capabilities for interaction with images and results and can be used to help clinicians confirm diagnoses and plan subsequent treatment steps.

Thus, the illustrative IDIS 300 can address the current limitations in medical imaging in one or more of the following ways:

Personalized Imaging: The system can enhance customization by enabling clinicians to identify specific diseases of interest for each patient via an intuitive, user-friendly interface. This selection can drive the tailoring of the imaging protocol to ensure that each patient's imaging process can be precisely adapted to be associated with their specific diagnostic needs.

Intelligent Automation: The protocol selection algorithm 322 can automatically select and implement an optimal imaging protocol to mitigate the risk of human error, remove the need for deep imaging expertise, and ensure consistency across varying patients and healthcare facilities. By determining the most efficient use of imaging resources and capturing only necessary images, the system can streamline the imaging process. This can result in significant advantages, including reducing the amount of time a patient spends in the imaging machine, minimizing unnecessary radiation exposure, improving the patient experience, and potentially decreasing overall healthcare costs.

AI-Enhanced Analysis: The system incorporates an advanced AI model registry 341 in the AI model selection system 340 that can utilize AI-based image analysis algorithms specifically developed for each disease of interest. These sophisticated algorithms can autonomously process and interpret the captured images to reduce reliance on expert interpretation and significantly accelerate the diagnostic process. Furthermore, the AI algorithms can aid in determining the appropriate imaging protocols by providing information to the system on which image types and protocols the algorithms perform best on, thus enhancing diagnostic accuracy through intelligent protocol selection.

Unified Workflow: The system can seamlessly fuse disease selection, imaging protocol determination, and image interpretation processes to create a cohesive, efficient diagnostic workflow. It can optimize each step to reduce redundancies, improve the overall user experience, and accelerate the entire diagnostic process to ultimately enhance patient care.

Adaptive Machine Learning: With its ability to continuously learn and improve from imaging data, the system can represent a dynamic machine learning model. Incorporating techniques such as active learning and reinforcement learning algorithms, the system can adaptively select the best imaging protocol based on past data and ongoing trends. This can ensure the system is always equipped with most accurate, up-to-date knowledge base, thereby progressively enhancing diagnostic capabilities.

Scalable Infrastructure: The system can be designed to integrate easily with existing imaging systems and hospital management systems, electronic medical records, and remote imaging facilities. By utilizing containerization, the system can allow for seamless scalability across multiple sites and systems. The architecture's modularity can ensure that the system can easily be upgraded or expanded, making it future-proof and adaptable to evolving diagnostic needs. The system's scalability could be amplified through federated learning, where the AI models can be trained on various local nodes, thereby allowing the system to benefit from geographically dispersed data while avoiding data centralization.

The system offers a comprehensive and flexible solution for disease screening through medical imaging. By leveraging advancements in AI and data-driven approaches with a focus on total process integration and modularity, the system can overcome many of the limitations and challenges of current medical imaging practices and can have the potential to significantly improve diagnostic accuracy, efficiency, and patient outcomes.

Disease Selection Interface

Figure 4:
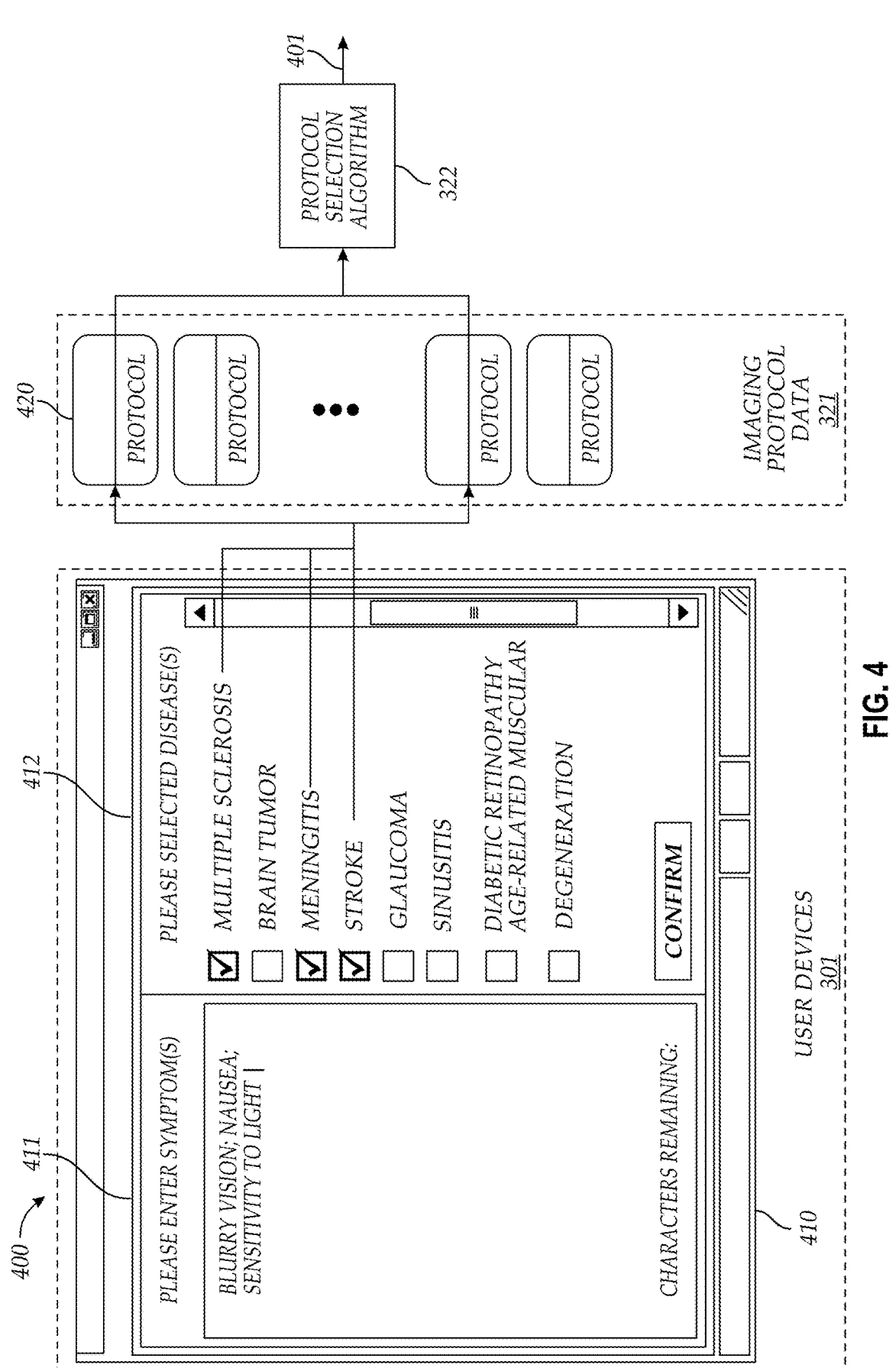
FIG. 4 is a block diagram of an illustrative combined imaging protocol system within the IDIS that determines a combined imaging protocol based on relevant imaging protocols related to the diseases selected on the same user devices.

FIG. 4 is a block diagram of an illustrative combined imaging protocol system 400 within the IDIS 300 that determines a combined imaging protocol based on relevant imaging protocols related to the diseases selected on the same user device 301. The Disease Selection Interface (DSI 410) can function as the initial interaction point between the clinician and the IDIS 300. The DSI 410 can be implemented through various user devices 301 to show a range of selectable conditions. A user can input health selections into the DSI 410 to output one or more diseases for the IDIS 300. These health selections can include, but are not limited to, diseases, symptoms, health history, patient details, or descriptions. This user device's 301 interfaces can be an application developed in a high-level programming language, capable of execution on an array of computing devices including but not limited to desktop computers, laptops, tablets, an interface on the imaging system such as a retina camera 100, and a smartphone, contingent on the design specifics of the system.

The application's architecture might be modular and event-driven, with an intuitive graphical user interface (GUI). It can incorporate algorithms to minimize the learning curve for users, focusing on providing efficient workflows for clinicians. The interface might also include internationalization and localization capabilities, thereby being adaptable for use in various regions and languages.

In enhancing its versatility, the DSI 410 can integrate with Electronic Health Record (EHR) systems using protocols, such as HL7 or FHIR. This integration might employ a secure API, enabling the interface to query the EHR and retrieve relevant patient details and medical history. Such an automatic data population can simplify the disease selection process and reduce the need for manual data entry.

The DSI 410 can provide user input of the health selections through a natural language processing query 411 and/or a list query 412. The natural language processing query 411 can operate by utilizing natural language processing (NLP) algorithms to interpret free-text symptom descriptions entered into the DSI 410. The list query 412 can operate by providing a list of health selections for a user to select. In some implementations, the list query can be in response to the natural language processing query 411 to provide a list of diseases that manifest the symptoms inputted in the natural language processing query 411. This interface can include a symptom-based selection mechanism. An AI-enabled differential diagnosis engine can process the natural language descriptions, or symptoms, along with other patient factors such as age, gender, medical history, and risk factors. The engine can then generate a tailored list of potential diseases manifesting the symptoms inputted to the DSI 410. This engine can then generate a tailored list of potential diagnoses and associated imaging protocols for a particular disease, potentially streamlining the protocol selection process. In some instances, the DSI 410 can use only a natural language processing query 411 or a list query 412. In some cases, the DSI 410 can use both the natural language processing query 411 and list query 412 and/or duplicates of either query for multi-layered queries of the various health selections. For example, the DSI 410 can include a health history list query 412, a health condition natural language processing query 411, a symptom list query 412, and a disease list query 412. In some implementations, the DSI 410 can use include multiple layers of list queries 412.

The main screen of the DSI 410 can present a categorized list of diseases and symptoms, possibly organized in a database-driven, dynamic tree structure. This tree can be manipulated in various ways, such as by body system, type of disease, type of symptoms, or based on the patient's medical history. The disease and symptom list can be presented as a dynamic, responsive grid or table, where each disease or symptom can be represented by a selectable UI element. This element can be instantiated as a checkbox, a switch, a dropdown menu, or another control suitable for multi-selection, depending on the desired user interaction model. A search bar, possibly equipped with a predictive text and autocorrect features enabled by a language processing algorithm, can be included to streamline the disease or symptom selection process.

After disease or symptom selection is finalized, a 'Submit' button, 'Confirm' button, or similar command, linked with an event handler can be used to trigger the Protocol selection algorithm 322. During this process, a loading or progress indicator generated through asynchronous programming techniques might be displayed.

The DSI 410 can be designed using cross-platform development tools to ensure compatibility with multiple operating systems (e.g., Windows, MacOS, Linux, Android, IOS) and might also adhere to WCAG accessibility guidelines. The software should follow HIPAA regulations to help ensure patient data privacy and security, perhaps implementing encryption protocols and secure user authentication methods.

Imaging Protocol Database

Continuing from the selected disease in FIG. 4, the protocol selection system 320 can include an imaging protocol database 321, which stores store imaging protocols 420, and a protocol selection algorithm 322, which identifies the optimal imaging protocol for each of the selected diseases and combines them into a combined imaging protocol. The imaging protocol database 321 can store information about the imaging protocols associated with each disease the system can screen for. Each disease can have one or more imaging protocols 420 associated with it. The database might be set up using an RDBMS such as PostgreSQL, MySQL, or Oracle, or it can be a NoSQL database like MongoDB, depending upon the requirements of scalability and the nature of data relations. The database schema can be designed such that each disease identifier maps to one or more imaging protocols 420, with each protocol further characterized by a unique set of parameters including but not limited to imaging modality, specific machine settings, and contrast agent use.

Each entry in the database can correspond to a specific disease and includes details about the most suitable imaging modality and parameters for detecting that disease. For example, an entry for "Pulmonary Embolism" can specify that the optimal imaging modality can be a CT scan, with specific settings for a CT Pulmonary Angiography (CTPA) protocol.

The database's structure can allow for efficient querying and updating. Each disease can be given a unique identifier or key, facilitating rapid search and retrieval of relevant information. In the case of a relational database structure, the database might consist of several linked tables, including a "Disease" table, an "Imaging Modality" table, and an "Imaging Parameters" table. This structure can allow for easy updates or additions to the imaging protocols while maintaining data consistency.

An illustrative example of one potential structure of the "Disease" table can be:

| Disease_ID | Disease_Name | Modality_ID |
|---|---|---|
| D1 | Multiple Sclerosis | M1 |
| D2 | Alzheimer's Disease | M1 |
| D3 | Brain Tumor | M1 |
| D4 | Parkinson's Disease | M1 |
| D5 | Pulmonary Embolism | M2 |
| D6 | Sinusitis | M2 |
| D7 | Diabetic Retinopathy | M3 |
| D8 | Age-related Macular Degeneration | M3 |
| D9 | Glaucoma | M3 |
| D9 | Glaucoma | M4 |

An illustrative example of one potential structure of the "Imaging Modality" Table can be:

| Modality_ID | Modality_Name |
|---|---|
| M1 | MRI |
| M2 | CT Scan |
| M3 | Color Retinal Photography |
| M4 | Optical Coherence Tomography |

An illustrative example of one potential structure of the "Imaging Parameters" Table can be:

| Disease_ID | Parameters |
|---|---|
| D1 | FLAIR and T2-weighted sequences, with and without contrast |
| D2 | T1- and T2-weighted sequences, with volumetric 3D sequence |
| D3 | T1-weighted sequences with and without gadolinium contrast |
| D4 | T2*-weighted sequences for detecting microbleeds |
| D5 | CTPA protocol |
| D6 | Head and Paranasal sinuses with contrast |
| D7 | Macula-centered |
| D8 | Macula-centered |
| D9 | Disk-centered |
| D9 | Peripapillary RNFL |

The specific imaging protocol 420 for a given disease or disease group can even be based on the performance of specific image analysis algorithms within the AI model selection system 340 for that specific disease or group of diseases to help determine which imaging protocols to call. The performance basis can be achieved by selecting imaging protocols 420 that increase the removal of redundancies. A combined imaging protocol can be optimized for both algorithmic diagnostic accuracy as well as efficiency.

The imaging protocol database 321 can be kept secure and backed up regularly to prevent data loss. Access to the database can be strictly controlled, with only authenticated system components (like the protocol selection algorithm 322) able to query or update the data. This approach can ensure patient privacy and system integrity. Depending on the imaging system and setup, this database can be stored in the cloud or in local memory.

Protocol Selection Algorithm

Continuing from the imaging protocol database 321 in FIG. 4, the protocol selection algorithm 322 interacts with the imaging protocol database 321 to retrieve the diseases selected via the DSI 410 and determines the optimal imaging protocols. The protocol selection algorithm 322 can identify which imaging protocols 420 are optimal for the selected diseases and then generate a combined imaging protocol based on them. In some implementations, an optimal imaging protocol for a selected disease can be one or more imaging protocols 420 with the least number of sequences or that has the largest number of redundancies with the imaging protocols 420 of the other selected diseases. In some instances, two diseases may share the same imaging protocol 420 because the redundancy would be all sequences for imaging protocol 420. The combined imaging protocol can be input (arrow 401) to imaging devices 330.

The protocol selection algorithm 322 can be implemented as a software function or module within the system's backend infrastructure. The protocol selection algorithm can be coded in a programming language such as Python, Java, or C++, depending on the overall system architecture and performance requirements. It can employ database interfacing libraries, such as JDBC for Java or SQLAlchemy for Python, to connect to the imaging protocol database 321.

In some instances, a high-level pseudocode representation of the protocol selection algorithm 322 querying the imaging protocol database 321 can be as follows:

```
function selectProtocol(diseaseList):
    imagingProtocols = [ ]
    for disease in diseaseList:
        protocol = queryDatabase(disease) // Retrieve the optimal imaging
            protocol for this disease
        imagingProtocols.append(protocol)
    if multiple protocols:
        imagingProtocols = sequenceProtocols(imagingProtocols) // Arrange
            multiple protocols for efficiency
    return imagingProtocols
```

The "queryDatabase(disease)" function can interact with the Imaging protocol database 321 to retrieve the optimal imaging protocol for a given disease. If multiple diseases are selected, requiring different imaging modalities or settings, the "sequenceProtocols(imagingProtocols)" function can arrange the protocols for maximum efficiency by removing redundancy. For example, it might sequence protocols to minimize the number of changes in imaging modality, remove overlap within different protocols so a sequence only occurs once in the combined imaging protocol, or it can prioritize certain protocols based on clinical urgency. This protocol selection algorithm 322 can also be designed with performance in mind, such as the removal of redundancy. It employs efficient data structures and algorithms to minimize response time, and it can handle high-load situations, such as a large number of disease selections or concurrent users, without significant performance degradation. As mentioned above, the protocol selection algorithm 322 can be an intelligent algorithm, which can be performance-oriented, so that an algorithm can optimize and implement the most efficient imaging protocols from the DSI 410 by reducing and/or removing redundancy in the combined imaging protocol based on the imaging modality and disease(s) of interest determined from the imaging protocol database 321. The removal of the redundancy can include but is not limited to, determining an overlap of the sequences between the relevant imaging protocols for the selected diseases and removing said overlap. In some implementations, the protocol selection system 320 can identify imaging protocols for a particular selected disease based on the redundancy with other potential imaging protocols for the other selected diseases in the DSI 410. The protocol selection system 320 can select the particular imaging protocol for each disease by selecting the sets or pairs of imaging protocols with the most number of redundancies, such that they exceed the number of redundancies of other potential sets or pairs of imaging protocols for the selected diseases. This can provide the protocol selection algorithm 322 with the imaging protocols that would remove the highest number of redundancies for the combined imaging protocol.

This protocol selection algorithm 322 can be dynamic, allowing for the addition of new diseases and corresponding imaging protocols 420 in the imaging protocol database 321. It can also be designed to be robust, handling invalid or incomplete disease selections and other potential errors gracefully, ensuring the system's continued operation.

Imaging System

Figure 5:
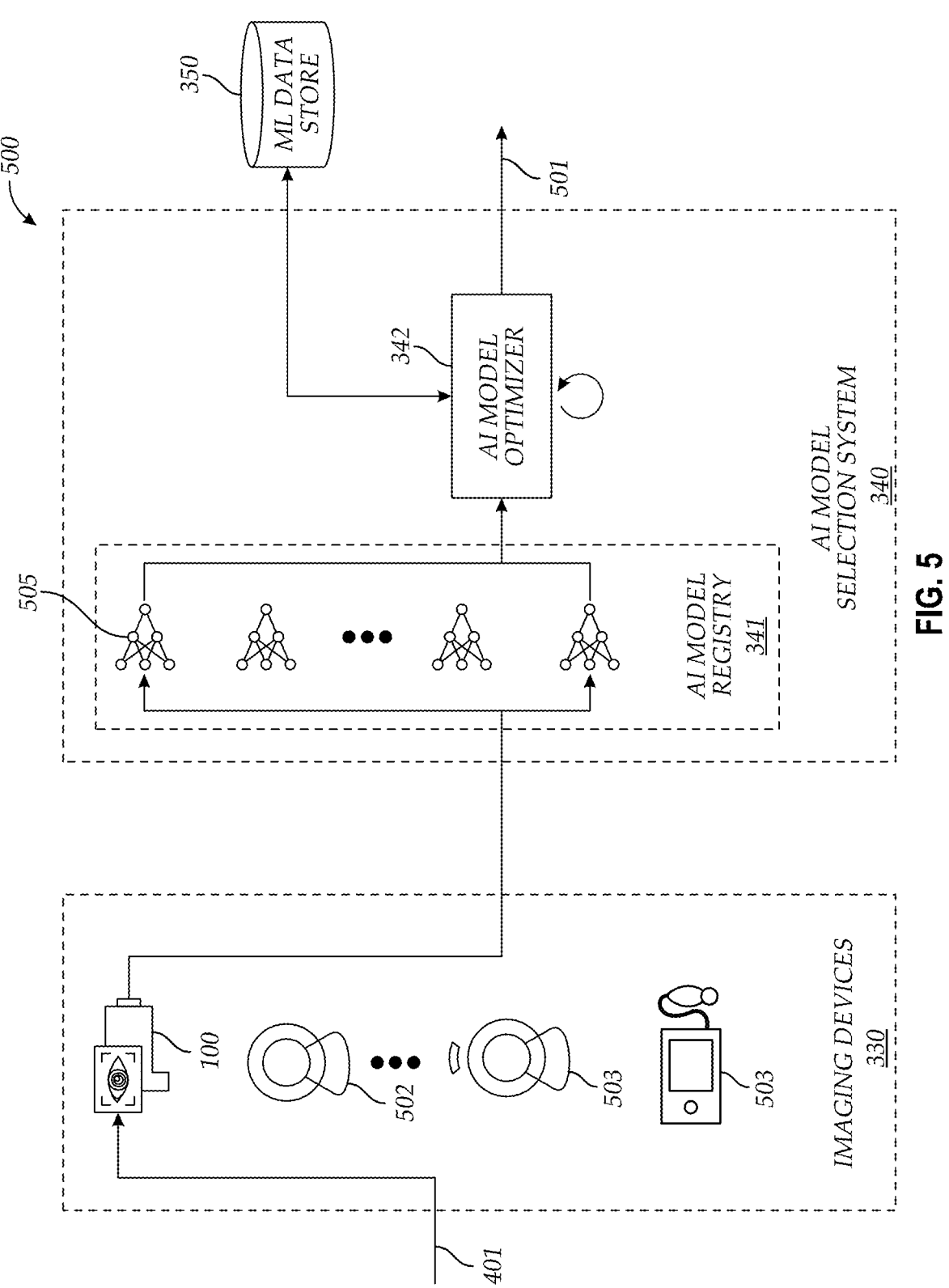
FIG. 5 is a block diagram of an illustrative image analysis system within the IDIS that obtains images according to the combined imaging protocol and analyses said images with a classifier.

FIG. 5 is a block diagram of an illustrative image analysis system 500 within the IDIS 300 that obtains images according to the combined imaging protocol and analyses of said images with a classifier. The imaging devices 330, or imaging modalities, in the IDIS 300 can be the hardware that obtains the necessary images based on the combined imaging protocol determined by the protocol selection system 320. The imaging devices 330 can potentially include a variety of hardware to obtain images such as but not limited to, the user devices 301, retinal imaging devices (such as, the retina camera 100), computed tomography (CT) scanners 502, magnetic resonance imaging (MRI) scanners 503, ultrasound devices 504, optical coherence tomography devices, color photography apparatus, and other imaging modalities predicated upon the system's capabilities and the protocol selection algorithm's 322 determination. In some implementations, the combined imaging protocol can require more than one imaging device 330.

Regardless of the selected modality, each imaging system can incorporate a sophisticated computerized control system, such as described in FIG. 2. This system can be engineered with a distributed computing architecture, possibly including local microcontrollers to control specific hardware subsystems and a central processor to coordinate overall imaging activities. The control system might be capable of receiving and decoding instructions transmitted from the IDIS via protocols, such as HL7 or DICOM.

The instructions received can contain detailed protocol parameters determined by the protocol selection algorithm 322, dictating the modality, equipment settings, imaging sequences, and other key attributes. Additionally, the protocol parameters can carry patient-specific information such as physical dimensions, allergies, or prior medical history that might necessitate adjustments to the imaging procedure.

Interpreting these instructions, the control software can utilize a combination of rule-based logic and machine-learning algorithms to set the required parameters. For example, if a T2-weighted sequence MRI is required, the control software could dynamically manipulate hardware settings such as but not limited to magnetic field strength, pulse sequence timing (for example, in milliseconds), slice thickness (for example, in millimeters), etc.

The imaging system could then perform obtaining the imaging, either autonomously or with the help of a trained imaging operator. In autonomous mode, the system can use built-in sensors and control algorithms to position the patient correctly, start the imaging at the appropriate time, and ensure the necessary images are captured. In operator-assisted mode, the operator could receive clear instructions from the system about what needs to be done and can manually control certain aspects of the imaging process.

After imaging, the software can bundle the images into the DICOM format, embedding metadata like patient demographics and imaging parameters. It can then use a secure communication protocol, such as DICOM's C-STORE service or a secure version of FTP, to transmit the images to the appropriate image analysis algorithms invoked from the AI model registry 341 for further processing.

The imaging device 330 can be integrated effectively with the other components of the IDIS to ensure obtaining high-quality images from optimized protocols that allow for accurate disease detection by the image analysis algorithms. In some implementations, the redundancies in the intelligent algorithm in the protocol selection algorithm 322 can include one or more of the following but are not limited to: changes between the imaging devices 330, the amount of radiation from the imaging devices 330, the overall duration of the combined imaging protocol using the imaging devices 330, and/or arrangement of the imaging devices based on clinical urgency.

AI Model Selection System

Continuing in FIG. 5 and after the images have been obtained by the imaging devices 330, the images can be analyzed by the AI model selection system 340. The AI model selection system 340 can include the AI model registry 341, which stores the image analysis algorithms 505 (and/or models) used to process the images for different diseases, and the 342, which determines a classifier based on the image analysis algorithms 505 for each selected disease. The AI model registry 341 houses the image analysis algorithms for each disease. The AI model optimizer 342 generates a classifier through machine learning models and/or artificial intelligence models by determining the selection of specific image analysis algorithms 505 and their execution for the selected diseases. The generated algorithm analyzes the images obtained by the imaging devices 330 to provide an indication of the selected diseases. This process commences once the imaging devices 330 has completed acquiring the images according to the protocols provided by the protocol selection algorithm 322. In some implementations, the AI model optimizer 342 will optimize the selected image analysis algorithms 505, such as by removing redundancy or by inputting the image analysis algorithms 505 into the ML database 350 to train an ideal analysis algorithm. In some instances, each image analysis algorithms 505 is already trained and combined together by the AI model optimizer 342.

The selection of image analysis algorithms 505 can be informed by the initial disease targets selected by the clinician via the DSI 410. However, it should be noted that while some diseases can have a dedicated model, other diseases can be detected by a more generalized model that has been trained to identify multiple diseases. For example, if the clinician has selected "Stroke," "Brain Tumor," and "Multiple Sclerosis" as disease targets, the system can load a general "BrainDiseaseModel" that has been trained to detect all three conditions. Alternatively, and depending on the specific algorithmic development approach, each disease can have its own dedicated model, for example, "Stroke- Model," "BrainTumorModel," or "MSModel." These models can be stored in the AI model registry 341, which can be local or cloud-based, depending on the system architecture.

To interface with the AI model registry 341, the protocol selection algorithm 322 can use frameworks like TensorFlow Serving or the NVIDIA Triton Inference Server. These frameworks can serve multiple models concurrently, manage model versioning, and allow for model updates without interrupting the service. The AI model registry 341 might store models in a format suitable for the chosen serving framework. For TensorFlow models, this can be the SavedModel format, and for PyTorch, the TorchScript format can be used. The AI model registry 341 can be structured to map each imaging protocol 420 to one or more image analysis algorithms 505, with each image analysis algorithms 505 designed to analyze images produced by the respective imaging protocols 420.

Communication between the protocol selection algorithm 322 and the AI model registry 341 can take place using HTTP/2 or gRPC protocols, with requests and responses structured as per the framework's specifications. These communication protocols can enable bi-directional streaming, flow control, and multiplexing requests over a single TCP connection, offering speed and efficiency in model serving.

The interaction between the protocol selection algorithm 322, the imaging protocol database 321, AI model optimizer 342, and the AI model registry 341 can be facilitated through a middleware component, possibly implemented in a language like Node.js or Go. This middleware can handle requests and responses between the protocol selection algorithm 322 and the other components, effectively managing data flow, error handling, and potential concurrency issues.

The entire system can be deployed and orchestrated using containerization tools like Docker and Kubernetes. This can allow for a scalable, fault-tolerant, and easily maintainable system capable of handling real-world loads and complexities.

A high-level pseudocode representation of the AI model optimizer 342 calling a specific singular image analysis algorithm 505 from the AI model registry 341 can be as follows:

```
function runModels(image, diseaseList):
    results = [ ]
    for disease in diseaseList:
        model = loadModel(disease) # Retrieve the appropriate model for this
            disease from the Model Database
        processedImage = preprocessImage(image, model) # Perform any
            necessary preprocessing specific to the model
        diagnosis = model.predict(processedImage) # Run the model on the
            preprocessed image
        explanation = model.explain(processedImage) #Generate an
            explanation for the model's decision
        results.append(diagnosis)
        explanations.append(explanation)
    return results, explanations
```

In this pseudocode, the "loadModel(disease)" function retrieves the appropriate machine learning model for the disease in question from the AI model registry 341, while "preprocessImage(image, model)" performs any necessary preprocessing on the image to prepare it for analysis. This preprocessing can include resizing the image, adjusting the contrast, extracting certain features, etc., and it can vary from model to model. The "model.predict(processedImage)" function then applies the model to the preprocessed image to produce a diagnosis. The "model.explain(processedImage)" function generates an explanation for the diagnosis made by the model. This explanation could be a visualization of the saliency maps, a list of most important features that the model considered, or a textual description of why the model made its decision.

This approach can ensure that the analysis can be suitable for the selected disease targets. Advantageously, this can encourage high diagnostic accuracy and enables the system to handle a broad range of disease targets flexibly.

Each image analysis algorithm 505 or model can be trained, validated, and tested using a distinct dataset to ensure its generalization capability. The models can be subject to periodic re-training with updated data to maintain their efficacy. Techniques like dropout, batch normalization, or data augmentation can be used during the training phase to prevent overfitting and improve model performance. Each image analysis algorithm or model can be trained, validated, and tested to ensure to detect features of a particular disease in the images obtained by the imaging devices 330. Thus, for each selected disease, the classifier can include a particular image analysis algorithm or model for each said selected diseases. In some implementations, the selection of the image analysis algorithms and generation of the classifier can include the removal of redundancies similar to the protocol selection system 320.

The image analysis algorithms 505 and AI model optimizer 342 can employ techniques ranging from image processing methods to sophisticated deep learning architectures, such as Convolutional Neural Networks (CNNs), Autoencoders, Transformers or Generative Adversarial Networks (GANs). These models can utilize transfer learning or fine-tuning approaches if pretrained models like ResNet, VGG, or Inception are used.

As new models are developed or as existing models are updated, the AI model registry 341 can be readily updated. This ensures that the system remains adaptable and up-to-date with the latest advances in medical image analysis. These updates update the entire IDIS 300, including the imaging protocol database 321, as new models can have different optimal protocols to achieve maximal performance.

Results Display

Figure 6:
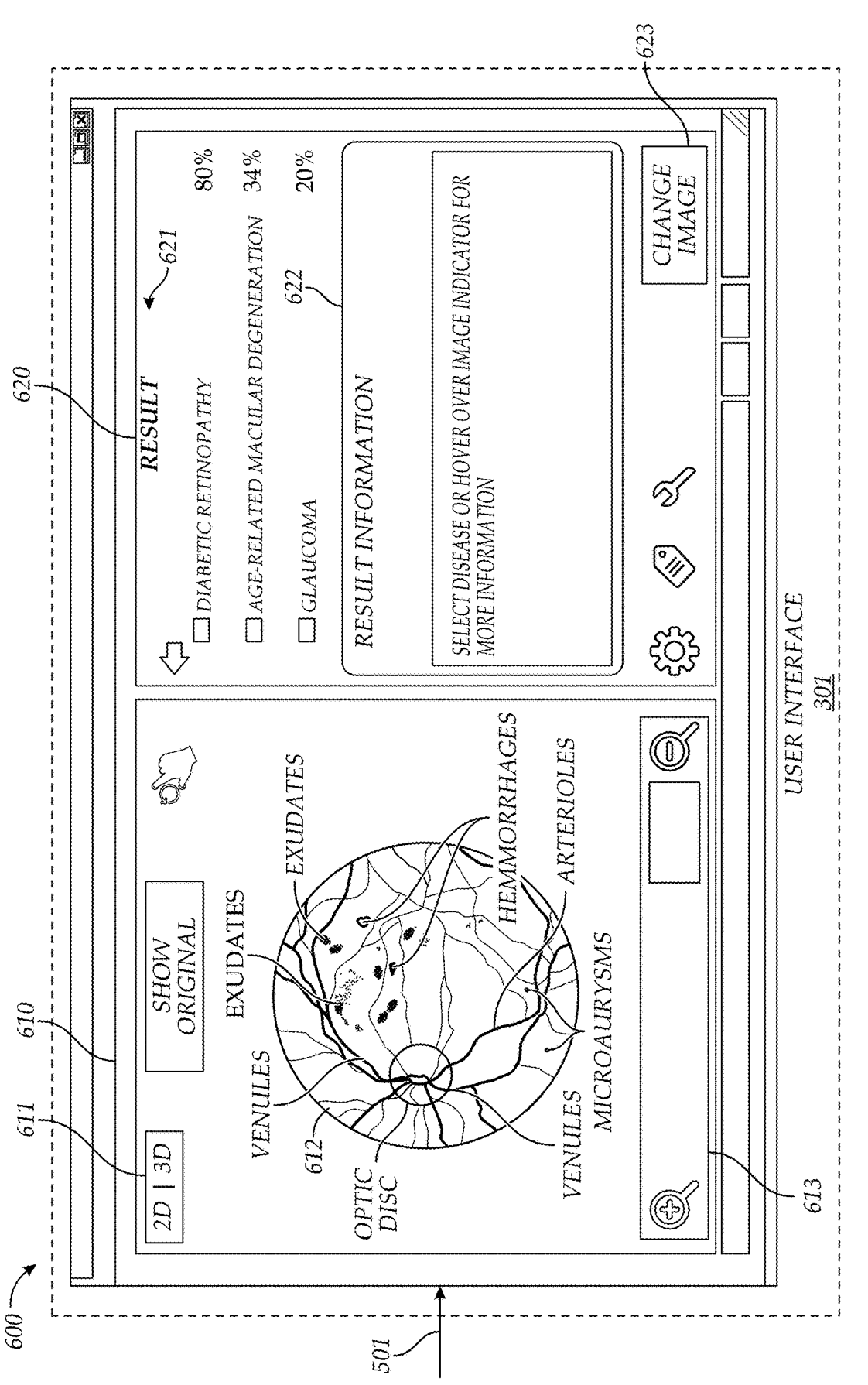
FIG. 6 is an example user interface of a results display within the IDIS that illustrates an indication of the presence of the selected diseases in a retina image.

FIG. 6 is an example user interface of a results display 600 within the IDIS 300 that illustrates an indication of the presence of the selected diseases from a retina image. The results display 600, outputted 501 from the AI model selection system 340, which can illustrate a comprehensive report of potential disease indicators, each linked with the corresponding image captured by the imaging devices 330. After the specific image analysis algorithms 505 or ideal image analysis algorithm have processed the images and produced diagnostic results, these results can be presented to the clinician on the results display 600. The results display 600 can be implemented on the user device 301, on the imaging devices 330, or on a separate device. The results display 600 can provide users or clinicians with an easy-to-understand representation of the patient's condition based on the AI model selection system 340.

The results display 600 can be a graphical user interface (GUI) that can be implemented on a standalone computer monitor, a portable device like a tablet, or even a web-based interface that can be accessed from any internet-connected device. The primary goal can be to present the results in a clear, intuitive, and actionable format for the clinician.

The GUI can be designed with user experience (UX) principles in mind, ensuring that clinicians can easily understand and act upon the results. For example, positive detections of the selected diseases might be highlighted in a distinct color or accompanied by an alert symbol.

The results display 600 can also allow clinicians to interact with the analyzed images 610 and the results 620. For instance, they might be able to zoom in or out of images 613, rotate 3D images 611, adjust image brightness or contrast, or click on areas or regions of interest 612 for more information. The display can show the original images 611 with relevant areas highlighted for the regions of interest 612, indications of the selected diseases 621, and a textual summary 622 of the algorithm's findings. Furthermore, the clinician can shuffle between different images 623. This information aids clinicians in confirming the diagnosis and planning the patient's subsequent treatment steps.

This comprehensive diagnostic imaging system can either be a standalone solution or integrated within a broader health information system. Ultimately, this system can represent a significant advancement in the field of medical imaging and diagnostics.

Some examples for how this IDIS can be implemented to improve medical imaging and disease screening are described herein.

Example: Retinal Camera for Retinal Disease Screening

One example application of the illustrative combined imaging protocol system 400 can be in a healthcare environment with a retinal camera 100 employed for retinal disease screening. The clinician can interact with the DSI 410 in the user device 303 through an intuitive touchscreen adjoined with the retinal camera 100. The DSI 410 can be populated with areas of interest 612, indicating retinal diseases that the retina camera 100 and the associated image analysis algorithms 505 are capable of screening for.

Given a patient's history, symptoms, and risk factors, the clinician opts to screen for diabetic retinopathy (DR) and glaucoma. In some implementations, the clinician can select DR and glaucoma after inputting symptoms that can manifest from DR and glaucoma. The clinician selects the corresponding checkboxes on the DSI 410, triggering the protocol selection algorithm 322.

The protocol selection algorithm 322 then accesses the imaging protocol database 321. This database can be equipped with imaging protocols 420 tailored for each disease, guiding the image acquisition process for the retinal camera 100.

To further exemplify this are two distinct scenarios as follows.

Scenario 1: Diabetic Retinopathy (DR) Screening

Suppose that the clinician intends to screen solely for DR, thereby selecting the "Diabetic Retinopathy" option on the DSI 410. Upon receiving this input, the protocol selection algorithm 322 queries the imaging protocol database 321 for the optimal imaging protocol for DR screening:

```
function selectProtocol(diseaseList):
    imagingProtocols = [ ]
    for disease in diseaseList:
        if disease == "Diabetic Retinopathy":
            protocol = {"device": "Retinal Camera", "views":
            ["macula-centered"], "images_per_eye": 1}
        imagingProtocols.append(protocol)
    return imagingProtocols
```

With "Diabetic Retinopathy" as the only entry in the 'diseaseList', this function can construct an imagingProtocols list that includes one imaging protocol 420, guiding the retinal camera 100 to capture one macula-centered image per eye 170. The optimal protocol in this case can be a single-macula centered imaged because the AI-based image analysis algorithms 505 can have previously been trained on this image type and found to have the highest diagnostic performance when provided a macula-centered retinal image as an input (compared to other views of the retina), and the diagnostic performance cannot meaningfully increase with additional images and views. Therefore, the optimal protocol for the DR algorithm can be a single, macula-centered image per eye. This can be stored in the imaging protocol database 321 and can be updated as the AI model registry 341 is updated.

Following the protocol selection algorithm, 322 may transmit this 'imagingProtocols' list to the retinal camera 100 through a suitable API call. For instance, the protocol selection algorithm 322 can send a POST request to the '/protocols' endpoint of the retina camera's 100 API, with the 'imagingProtocols' list included in the body of the request. The API of the retinal camera 100, upon receiving this request, can forward the 'imagingProtocols' list to the camera's internal control system 200.

In response to this information, the internal control system 200 of the retinal camera 100 can interpret the received 'imagingProtocols' list and adjust the camera's settings to comply with the imaging protocols 420. To capture a macula-centered image, the control system might light up a specific internal LED fixation target for the patient to gaze at during the imaging, thereby ensuring that the macula, a part of the retina often affected by DR, can be centered in the image. Moreover, the control system 200 can also configure the retina camera 100 to capture just one image per eye, in alignment with the 'imagingProtocols' list. This approach might help to minimize the duration and potential discomfort associated with the imaging process, as it avoids capturing any superfluous images.

Throughout this process, the protocol selection algorithm 322 and the retinal camera 100 can continue to communicate via their respective APIs, ensuring that the retina camera 100 acquires images according to the optimal protocol tailored for the selected diseases. Such a system can allow for a more flexible and efficient disease screening process, modifying the imaging protocol based on the individual requirements of each patient.

This efficiency of the image analysis algorithm generated by the AI model optimizer 342 and integration with the imaging devices 330 to implement the optimal protocol eliminates the need for additional images or views to be acquired and improves efficiencies and accuracy.

Scenario 2: Diabetic Retinopathy (DR) and Glaucoma Screening

Suppose that the clinician decides to screen for both "Diabetic Retinopathy" and "Glaucoma." The protocol selection algorithm 322 now amalgamates the imaging protocol suitable for both diseases:

```
function selectProtocol(diseaseList):
    imagingProtocols = [ ]
    for disease in diseaseList:
        if disease == "Diabetic Retinopathy":
            protocol = {"device": "Retinal Camera", "views":
                ["macula-centered"], "images_per_eye": 1}
        elif disease == "Glaucoma":
            protocol = {"device": "Retinal Camera", "views":
                ["disk-centered"], "images_per_eye": 1}
        imagingProtocols.extend([protocol_DR, protocol_G])
    return optimizeSequence (imagingProtocols) // Combine protocols for
efficiency
```

The retinal camera 100 receives this combined protocol and adjusts its settings to capture both a macula-centered image and a disk-centered image per eye. These images are optimal for the image analysis algorithms 505 generated by the AI model optimizer 342 specific to both DR and Glaucoma detection, ensuring accuracy. The acquired images are then processed by the image analysis algorithms 505 designed for DR and Glaucoma. These algorithms are trained to detect characteristic disease indicators such as microaneurysms and hemorrhages for DR, optic disk cupping, and retinal nerve fiber layer thinning for Glaucoma.

The detection results are conveyed via the results display 600, integrated within the retinal camera 100. The results display 600 renders the images captured by the retina camera 100, highlights the regions scrutinized by the image analysis algorithms 505, and showcases the detection results. Detailed feedback, such as the location and severity of detected anomalies, can be provided if signs of disease are detected.

This implementation reinforces the efficacy and adaptability of the IDIS 300 in varied disease screening contexts, as it enables a more streamlined, precise, and time-efficient screening process, enhancing the patient experience and boosting the healthcare provider's diagnostic capabilities. Optimizing image acquisition and AI-enhanced analysis minimizes redundancy and patient discomfort due to bright flashes, reduces imaging time, and supports clinicians in managing their workload effectively.

Example: MRI Machine for Brain Disease Screening

In a clinical setting example, a patient can present with non-specific neurological symptoms such as persistent headaches, memory problems, and balance issues into the natural language processing query 411 or list query 412 of the DSI 410. The attending clinician, suspecting a potential neurological condition, decides to utilize the IDIS 300. The differential diagnosis can include brain tumor, stroke, and normal pressure hydrocephalus, due to the overlapping symptomatology of these conditions.

The DSI 410 can be accessed through the clinician's computer or any other connected user device 301 or integrated into the MRI 503 itself. The DSI 410 interface can be user-friendly, presenting a categorically organized list of conditions, or groups of conditions, or signs and symptoms for a quick and easy disease of interest selection, the diseases manifesting the inputted signs and/or symptoms. In this case, the clinician can select "brain tumor," "stroke," and "normal pressure hydrocephalus" from the list of conditions.

Upon confirming the selection, protocol selection algorithm 322 can retrieve the specific imaging protocols 420 for these conditions from the imaging protocol database 321. Each imaging protocol 420 can specify the type and sequence of images to be captured by the MRI 503 machine. For instance, the database can recommend T1-weighted and T2-weighted imaging sequences for brain tumors, diffusion-weighted imaging for stroke, and T2-weighted and FLAIR sequences for normal pressure hydrocephalus.

The protocol selection algorithm 322 works to optimize the imaging protocol 420 by identifying redundancies across the imaging protocols 420 of the selected diseases and consolidating them. For example, if both brain tumor and normal pressure hydrocephalus require a T2-weighted sequence, the protocol selection algorithm 322 might consolidate these requirements and only include the T2-weighted sequence once in the final combined imaging protocol. This results in a combined imaging protocol that includes T1-weighted, T2-weighted, diffusion-weighted, and FLAIR imaging sequences.

To optimize sequence protocols further, the protocol selection algorithm 322 can implement an optimization algorithm such as a Greedy Algorithm, Genetic Algorithm, or a variant of a dynamic programming algorithm. These algorithms can consider factors like the minimum number of sequences required to screen for all selected diseases, the total scanning time, and the diagnostic performance of the AI models associated with each sequence.

Once the combined imaging protocol is determined, the MRI 503 machine can receive this protocol and adjust its settings, accordingly, setting up the necessary imaging sequences. The patient can be imaged once, with the MRI 503 machine adjusting the imaging parameters as needed for each sequence in a time-optimized manner.

Following the imaging session, the AI model registry 341 can access specific AI-based image analysis algorithms 505 to process the captured images. Each selected condition corresponds to a specific AI image analysis algorithm 505 or model trained to detect features indicative of that disease. For instance, the model for stroke detection might focus on areas of restricted diffusion, while the model for normal pressure hydrocephalus can look for enlarged ventricles.

The results from these algorithms are then displayed on the results display 600, providing a clear and concise report on potential disease indicators found in the imaging study. Each finding can be linked to the corresponding image 623, allowing the clinician to further investigate the finding.

This implementation can offer significant advantages over the traditional approaches. It can enable the clinician to efficiently screen for multiple conditions with one imaging session, with each condition utilizing the optimal imaging sequence and AI analysis for detection. It can reduce the expertise needed to determine the optimal sequences for each disease. The optimization of sequence protocols themselves not only decreases scanning time and increases patient comfort but can also reduce costs associated with the MRI 503 procedure and the data processing overhead for the AI models. Furthermore, it can enhance diagnostic accuracy and speed, providing actionable insights to the clinician in a timelier manner. Advantageously, the disclosed approaches represent a significant improvement over traditional medical imaging practices.

Example: CT Machine for Abdominal Disease Screening

In a healthcare setting example, a patient can present persistent abdominal discomfort and unexplained weight loss. The patient's clinical history and symptoms raise several potential concerns to the attending clinician, including liver disease, kidney stones, pancreatic cancer, and gallbladder disease. To screen for these potential conditions, the clinician employs the IDIS 300.

The DSI 410 can be accessed from the clinician's computer or any other connected user device 301. The clinician selects "liver disease," "kidney stones," "pancreatic cancer," and "gallbladder disease" from the categorically organized list of conditions available on the interface from the list query 412.

Upon confirmation, the protocol selection algorithm 322) can retrieve the specific imaging protocols 420 for these conditions from the imaging protocol database 321. For instance, the database might recommend a contrast-enhanced CT scan 502 for liver disease and pancreatic cancer, with specific phases post-contrast administration for optimal visualization. For kidney stones, the database might suggest a non-contrast CT scan, while for gallbladder disease, the protocol selection algorithm 322 might recommend both non-contrast and post-contrast phases.

The protocol selection algorithm 322 optimizes the imaging protocol by identifying commonalities/redundancies and differences in the recommended protocols. For example, it can consolidate these into a single protocol that includes both contrast-enhanced and non-contrast phases, along with optimized timing for post-contrast scanning to visualize each organ of interest effectively. This approach removes redundancy by reducing unnecessary radiation exposure and enhances patient comfort.

The optimized protocol can then be transmitted to the CT scan 502 machine via a secure network 310 connection. The CT scan 502 machine can adjust its settings accordingly, under the supervision of a radiologic technologist who assists with patient positioning and ensures patient safety throughout the procedure. The patient undergoes a single, optimally sequenced imaging session, thereby reducing their exposure to radiation.

Upon completion, the captured images are processed by specific AI-based image analysis algorithms 505 or a combined image analysis algorithm housed within the AI model registry 341. Each selected condition can correspond to specific AI image analysis algorithms 505 or models trained to detect features indicative of that disease. For instance, the model for liver disease might focus on changes in liver size, shape, or density, while the model for kidney stones can look for high-density objects within the kidneys. The models for pancreatic cancer and gallbladder disease can identify abnormalities such as masses, lesions, or changes in organ structure.

The findings of these AI image analysis algorithms 505 and/or models can then be displayed on the results display 600, which can be accessible from the clinician's computer or any other connected user devices 301. It provides a clear and concise report of the potential disease indicators found in the imaging study, with each finding linked to the corresponding image.

The system can be capable of selecting and consolidating multiple disease-specific imaging protocols into one optimized protocol, enhancing diagnostic accuracy, reducing unnecessary radiation exposure, and improving patient comfort. This system integrates AI and sophisticated algorithmic optimization, as well as providing comprehensive, accurate, and efficient diagnostic information in a clinical setting.

Example: Multi-Modality Imaging Optimization for Oncology Screening

In one example, a cancer survivor comes in for routine monitoring at an oncology clinic as a patient. Given this patient's history, the oncologist can screen for potential recurrence of primary cancer and detect any potential secondary metastasis.

The oncologist can access the DSI 410 on their office computer or any other connected user device 301, over a secure network 310, to ensure minimal disruption to the clinic's workflow. From this interface, the oncologist can select the original "lung cancer" and additional areas of potential metastasis, such as "brain," "liver," and "bone," from the list query 412.

Upon selection, the protocol selection algorithm 322 queries the imaging protocol database 321 to obtain the optimal imaging protocols 420 for each area of interest. For example, the protocol selection algorithm 322 might suggest a low-dose CT scan 502 for lung cancer, an MRI 503 for potential brain metastases, an ultrasound 504 or MRI 503 for liver lesions, and a bone scan or PET-CT for potential bone metastases.

The protocol selection algorithm 322 can employ a combination of techniques to optimize the imaging protocols 420. First, it can understand disease-specific requirements, as the protocol selection algorithm 322 can be well-informed about the specific imaging requirements for each disease. For example, for lung cancer, it may know that low-dose CT scans 502 can be effective for screening. On the other hand, for potential brain metastases, it can select MRI 503 as the imaging modality of choice due to its superior soft-tissue contrast. Second, it can optimize the imaging protocol sequence by determining the best sequence of imaging studies to remove redundancy and minimize patient movement and adjustments. For instance, if the patient needs both CT scans 502 and MRI 503 scans, it might schedule the MRI 503 first to avoid the interference that residual CT scan 502 contrast media might cause in subsequent MRI 503 scans. This way, the protocol selection algorithm 322 can take into account the physiological implications of each scan and its potential impact on subsequent ones. It can also consider scheduling optimization when optimizing imaging protocols. This can be especially important when contrast agents or radiotracers are needed, as these can require specific time intervals for optimal distribution within the body. The PSA, taking into account the half-life of the radiotracer, the type of contrast agent, and the organs to be imaged, can schedule PET-CT or contrast-enhanced studies at specific times to allow for peak distribution and uptake, thus maximizing image quality. The protocol selection algorithm 322 can also take into account patient-specific factors such as age, weight, and medical history. This might affect the choice of contrast agent, the dosage of the radiotracer, or the use of radiation shielding in certain cases. Furthermore, the protocol selection algorithm 322 can adjust the imaging protocol based on prior imaging studies, optimizing the protocol to capture new or additional data that might be crucial for diagnosis. Lastly, the protocol selection algorithm 322 can use AI and machine learning techniques to constantly update and refine the imaging protocols. As more data is accumulated from past scans and their outcomes, the protocol selection algorithm 322 can iteratively improve its protocol selection and optimization processes, driving better patient outcomes over time.

In some cases, such multi-faceted approach to optimization showcases the sophistication of the protocol selection algorithm 322. The result can be a streamlined, personalized, and efficient imaging process that aligns with the best practices in patient care and medical imaging.

The instructions from the protocol selection algorithm 322 can be inputted (as illustrated by arrow 401 in FIG. 4) to the respective imaging devices 330 in the clinic or hospital via a secure network 310. Imaging technologists can receive customized imaging protocols and perform the imaging sessions accordingly.

Once the images are obtained, they can be processed by the respective AI-based image analysis algorithms 505 within the AI model registry 341 and determined by the AI model optimizer 342. These disease-specific models analyze the images for signs of primary tumor recurrence or metastasis. The image analysis algorithms 505 are trained to identify subtle features indicating diseases, such as small nodules in the lung, lesions in the liver, abnormalities in the brain, or hotspots in bone scans.

The results from the AI image analysis algorithms 505 can be presented on the results display 600, accessed from the oncologist's workstation. The oncologist can receive a comprehensive report indicating potential areas of concern, linked with the corresponding images for further review.

This implementation emphasizes, particularly in the context of oncology follow-ups, where multiple organs might need to be screened using different imaging modalities. Advantageously, the ability to efficiently schedule and sequence different imaging studies using the PSA, alongside AI-assisted interpretation, can greatly enhance clinical workflow, patient comfort, and overall diagnostic efficiency. This implementation illustrates a distinct advancement over current practices.

Terminology

All of the methods and tasks described herein can be performed and fully automated by a computer-implemented system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or device (e.g., solid-state storage devices, disk drives, etc.). The various functions disclosed herein can be embodied in such program instructions or can be implemented in application-specific circuitry (e.g., ASICs or FPGAs) of the computer system. Where the computer system includes multiple computing devices, these devices may, but need not, be co-located. The results of the disclosed methods and tasks can be persistently stored by transforming physical storage devices, such as solid-state memory chips or magnetic disks, into a different state. In some embodiments, the computer system can be a cloud-based computing system whose processing resources are shared by multiple distinct business entities or other users.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, multiple processors or processor cores, or on other parallel architectures rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor (DSP), an application-specific integrated circuit (ASIC), a field programmable gate array (FPGA) or other programmable logic devices, discrete gate or transistor logic, discrete hardware components, or any combination thereof designed to perform the functions described herein. For example, a processor device can be a microprocessor, but in the alternative, the processor device can be a controller, microcontroller, or logic circuitry that implements a state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device can also include primarily analog components. For example, some or all of the rendering techniques described herein can be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, a software module executed by a processor device, or a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. Alternatively, the storage medium can be integral to the processor device. For example, the processor device and the storage medium can reside in an ASIC. The ASIC can reside in a user terminal. Alternatively, the processor device and the storage medium can reside as discrete components in a user terminal.

The conditional language used herein, such as, among others, "can," "can," "might," "may," "e.g.," and the like, unless specifically stated otherwise or otherwise understood within the context as used, is generally intended to convey that certain embodiments include, while other embodiments do not include certain features, elements or steps. Thus, such conditional language is not generally intended to imply that features, elements, or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive languages such as the phrase "at least one of X, Y, or Z," unless specifically stated otherwise, is otherwise understood with the context as used in general to present that an item, term, etc., can be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above-detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. Accordingly, the scope of certain embodiments disclosed herein is indicated by the appended claims rather than by the foregoing description. All changes which come within the meaning and range of equivalency of the claims are to be embraced within their scope.

What is claimed is:

1. A non-transitory computer readable medium storing instructions that, when executed by one or more processors, cause the one or more processors to perform a retinal imaging method comprising:

receiving one or more health selections from a user interface, wherein the one or more health selections comprise a selection of a first disease and a second disease from a plurality of diseases;

identifying a first imaging protocol associated with the first disease and identifying a second imaging protocol associated with the second disease from a plurality of imaging protocols, wherein the first imaging protocol and the second imaging protocol each specifies one or more retinal view identifiers for acquisition by a retinal imaging camera, the one or more retinal view identifiers comprising at least one of a macula-centered view identifier or an optic-disc-centered view identifier;

generating a combined imaging protocol based on combining the first imaging protocol and the second imaging protocol, the combining comprising removing a redundancy between the first and second imaging protocols, wherein the redundancy comprises a duplicate retinal view identifier specified by both the first imaging protocol and the second imaging protocol;

obtaining, with the retinal imaging camera, a plurality of images of a retina according to the combined imaging protocol, wherein obtaining the plurality of images comprises, based on the combined imaging protocol, (i) setting one or more parameters for imaging the retina comprising at least one of illumination, focus, aperture selection, or image capture, and (ii) selectively activating a fixation target of the retinal imaging camera comprising at least one light emitting diode to direct gaze for at least one retinal view identifier specified by the combined imaging protocol; and providing an indication of a presence of the first disease and the second disease based on analyzing the plurality of images of the retina, wherein analyzing comprises selecting, from a model registry, one or more image analysis algorithms associated with the first disease and the second disease and executing the selected one or more image analysis algorithms, wherein the one or more processors comprise one or more processors of the retinal imaging camera and one or more processors of a computing device configured to be communicatively coupled to the retinal imaging camera.

2. The non-transitory computer readable medium of claim 1, wherein the first imaging protocol comprises a first sequence of images and the second imaging protocol comprises a second sequence of images, and wherein the redundancy comprises an overlap between the first and second sequences of images.

3. The non-transitory computer readable medium of claim 2, wherein the identifying comprises selecting the first imaging protocol from a first plurality of imaging protocols associated with the first disease and selecting the second imaging protocol from a second plurality of imaging protocols associated with the second disease, and wherein the first and second imaging protocols are selected responsive to determining that the overlap between the first and second imaging protocols exceeds overlaps between other pairs of imaging protocols from the first and second pluralities of imaging protocols.

4. The non-transitory computer readable medium of claim 1, wherein the indication of the presence of the first disease and the second disease is performed by a classifier.

5. The non-transitory computer readable medium of claim 4, wherein the classifier comprises a machine learning model configured to detect in the plurality of images one or more features relevant to the first disease and the second disease.

6. The non-transitory computer readable medium of claim 1, wherein providing the indication comprises displaying the indication on a display.

7. The non-transitory computer readable medium of claim 1, wherein providing the indication comprises communicating the indication to a remote computing system.

8. A retinal imaging method comprising:

receiving one or more health selections from a user interface, wherein the one or more health selections comprise a selection of a first disease and a second disease from a plurality of diseases;

identifying a first imaging protocol associated with the first disease and identifying a second imaging protocol associated with the second disease from a plurality of imaging protocols, wherein the first imaging protocol and the second imaging protocol each specifies one or more retinal view identifiers for acquisition by a retinal imaging camera, the one or more retinal view identifiers comprising at least one of a macula-centered view identifier or an optic-disc-centered view identifier;

generating a combined imaging protocol based on combining the first imaging protocol and the second imaging protocol, the combining comprising removing a redundancy between the first and second imaging protocols, wherein the redundancy comprises a duplicate retinal view identifier specified by both the first imaging protocol and the second imaging protocol;

obtaining, with the retinal imaging camera, a plurality of images of a retina according to the combined imaging protocol, wherein obtaining the plurality of images comprises, based on the combined imaging protocol, (i) setting one or more parameters for imaging the retina comprising at least one of illumination, focus, aperture selection, or image capture, and (ii) selectively activating a fixation target of the retinal imaging camera comprising at least one light emitting diode to direct gaze for at least one retinal view identifier specified by the combined imaging protocol; and providing an indication of a presence of the first disease and the second disease based on analyzing the plurality of images of the retina, wherein analyzing comprises selecting, from a model registry, one or more image analysis algorithms associated with the first disease and the second disease and executing the selected one or more image analysis algorithms, wherein the retinal imaging method is performed by one or more processors of the retinal imaging camera and one or more processors of at least one computing device communicatively coupled to the retinal imaging camera.

9. The retinal imaging method of claim 8, wherein the first imaging protocol comprises a first sequence of images and the second imaging protocol comprises a second sequence of images, and wherein the redundancy comprises an overlap between the first and second sequences of images.

10. The retinal imaging method of claim 9, wherein the identifying comprises selecting the first imaging protocol from a first plurality of imaging protocols associated with the first disease and selecting the second imaging protocol from a second plurality of imaging protocols associated with the second disease, and wherein the first and second imaging protocols are selected responsive to determining that the overlap between the first and second imaging protocols exceeds overlaps between other pairs of imaging protocols from the first and second pluralities of imaging protocols.

11. The retinal imaging method of claim 8, wherein the indication of the presence of the first disease and the second disease is performed by a classifier.

12. The retinal imaging method of claim 11, wherein the classifier comprises a machine learning model configured to detect in the plurality of images one or more features relevant to the first disease and the second disease.

13. The retinal imaging method of claim 8, wherein providing the indication comprises displaying the indication on a display.

14. The retinal imaging method of claim 8, wherein providing the indication comprises communicating the indication to a remote computing system.

* * * * *